(12) United States Patent
Pascual et al.

(10) Patent No.: US 9,452,205 B2
(45) Date of Patent: Sep. 27, 2016

(54) **RECOMBINANT *LACTOCOCCUS LACTIS* EXPRESSING *ESCHERICHIA COLI* COLONIZATION FACTOR ANTIGEN I (CFA/I) FIMBRIAE AND THEIR METHODS OF USE**

(71) Applicant: MONTANA STATE UNIVERSITY, Bozeman, MT (US)

(72) Inventors: David W. Pascual, Bozeman, MT (US); Massimo Maddaloni, Bozeman, MT (US)

(73) Assignee: Montana State University, Bozeman, MT (US)

( * ) Notice: Subject to any disclaimer, the term of this patent is extended or adjusted under 35 U.S.C. 154(b) by 0 days.

(21) Appl. No.: 14/035,070

(22) Filed: Sep. 24, 2013

(65) Prior Publication Data

US 2014/0086950 A1    Mar. 27, 2014

Related U.S. Application Data

(60) Provisional application No. 61/704,672, filed on Sep. 24, 2012.

(51) Int. Cl.
*A61K 35/74* (2015.01)
*C12N 1/21* (2006.01)
(Continued)

(52) U.S. Cl.
CPC ......... *A61K 39/0258* (2013.01); *A61K 35/744* (2013.01); *A61K 35/747* (2013.01); *A61K 2039/523* (2013.01); *A61K 2039/58* (2013.01)

(58) Field of Classification Search
CPC .............................. C12N 15/74; A61K 39/00

USPC .................................... 424/200.1; 435/252.9
See application file for complete search history.

(56) References Cited

U.S. PATENT DOCUMENTS

| 5,426,047 A | * | 6/1995 | Ito | C12N 15/746 435/252.3 |
| 5,837,509 A | * | 11/1998 | Israelsen | C12N 15/746 435/257.3 |

(Continued)

FOREIGN PATENT DOCUMENTS

| CN | 10116874 | * | 4/2008 | C12N 15/74 |
| CN | 102031262 | * | 4/2011 | C12N 15/31 |

(Continued)

OTHER PUBLICATIONS

Li, Yong-Fu et al, Structure of CFA/I fimbriae from enterotoxigenic *Escherichia coli*, PNAS, Jun. 30, 2009, vol. 106(26), pp. 10793-10798.*

(Continued)

*Primary Examiner* — Albert Navarro
*Assistant Examiner* — Ginny Portner
(74) *Attorney, Agent, or Firm* — Cooley LLP

(57) ABSTRACT

The present disclosure relates generally to therapeutic compositions comprising recombinant bacteria. Further, the disclosure elaborates upon methods of utilizing the taught therapeutic compositions to treat autoimmune and inflammatory disease. The present teachings also relate to the disclosed recombinant bacteria and methods of producing the recombinant bacteria utilized in the compositions and methods. Further taught herein are dietary supplements and food additive compositions comprising the taught recombinant bacteria.

23 Claims, 10 Drawing Sheets

(51) Int. Cl.

| | | |
|---|---|---|
| *A61K 39/21* | (2006.01) | |
| *A61K 39/108* | (2006.01) | |
| *A61K 35/747* | (2015.01) | |
| *A61K 35/744* | (2015.01) | |
| *A61K 39/00* | (2006.01) | |

(56) References Cited

U.S. PATENT DOCUMENTS

| | | | |
|---|---|---|---|
| 5,874,088 A * | 2/1999 | Mekalanos | 424/200.1 |
| 5,914,248 A * | 6/1999 | Kuipers | A23C 9/1238 |
| | | | 435/252.3 |
| 5,928,900 A * | 7/1999 | Masure | C07K 14/3156 |
| | | | 424/185.1 |
| 6,100,388 A * | 8/2000 | Casas et al. | 536/23.5 |
| 6,159,465 A * | 12/2000 | Adlerberth et al. | 424/93.45 |
| 6,190,662 B1 * | 2/2001 | Steidler | C07K 14/31 |
| | | | 424/184.1 |
| 6,902,743 B1 | 6/2005 | Setterstrom et al. | |
| 7,422,747 B2 * | 9/2008 | Langridge et al. | 424/184.1 |
| 7,495,092 B2 * | 2/2009 | Barrangou et al. | 536/24.1 |
| 7,527,802 B2 | 5/2009 | Glenn et al. | |
| 7,759,106 B2 * | 7/2010 | Ranallo | A61K 39/0258 |
| | | | 424/184.1 |
| 7,829,104 B2 | 11/2010 | Sun et al. | |
| 7,943,122 B2 | 5/2011 | Turner et al. | |
| 8,293,230 B2 * | 10/2012 | Rummel | 424/94.63 |
| 2001/0014668 A1 * | 8/2001 | Cassels et al. | 514/14 |
| 2002/0012637 A1 * | 1/2002 | Neeser et al. | 424/50 |
| 2002/0076706 A1 * | 6/2002 | Duffner et al. | 435/6 |
| 2002/0176868 A1 * | 11/2002 | Altboum et al. | 424/190.1 |
| 2003/0138775 A1 * | 7/2003 | Le Page et al. | 435/6 |
| 2003/0170264 A1 | 9/2003 | Turner et al. | |
| 2004/0005662 A1 * | 1/2004 | Cassels | A61K 39/0258 |
| | | | 435/69.1 |
| 2004/0009937 A1 * | 1/2004 | Chen et al. | 514/44 |
| 2004/0156829 A1 * | 8/2004 | Wolf et al. | 424/93.2 |
| 2004/0209367 A1 | 10/2004 | Charles et al. | |
| 2004/0253710 A1 * | 12/2004 | Turner et al. | 435/252.3 |
| 2005/0054075 A1 * | 3/2005 | Turner et al. | 435/243 |
| 2005/0075298 A1 * | 4/2005 | Chen | A61K 35/741 |
| | | | 514/44 R |
| 2005/0186666 A1 * | 8/2005 | Schneider | C12N 9/0028 |
| | | | 435/108 |
| 2006/0153878 A1 * | 7/2006 | Savarino | A61K 39/0258 |
| | | | 424/241.1 |
| 2006/0165716 A1 * | 7/2006 | Telford | A61K 39/0208 |
| | | | 424/190.1 |
| 2007/0031458 A1 * | 2/2007 | Favre | A61K 39/0258 |
| | | | 424/261.1 |
| 2007/0237791 A1 * | 10/2007 | Ranallo | A61K 39/0258 |
| | | | 424/234.1 |
| 2007/0248573 A1 * | 10/2007 | Sturino | A61K 35/76 |
| | | | 424/93.6 |
| 2007/0299008 A1 * | 12/2007 | Rummel | 514/12 |
| 2008/0038319 A1 * | 2/2008 | Wolf et al. | 424/439 |
| 2008/0254058 A1 * | 10/2008 | Glenting et al. | 424/197.11 |
| 2009/0081166 A1 * | 3/2009 | Lebens | A61K 39/0258 |
| | | | 424/93.2 |
| 2009/0136567 A1 * | 5/2009 | Savarino et al. | 424/463 |
| 2010/0080774 A1 * | 4/2010 | Steidler et al. | 424/93.2 |
| 2010/0104601 A1 * | 4/2010 | Rottiers | A61K 39/0008 |
| | | | 424/234.1 |
| 2010/0136059 A1 * | 6/2010 | Lebens | C12N 15/70 |
| | | | 424/257.1 |
| 2010/0150943 A1 * | 6/2010 | Grandi | A61K 39/092 |
| | | | 424/165.1 |
| 2010/0178273 A1 * | 7/2010 | Rottiers | 424/93.2 |
| 2011/0020866 A1 * | 1/2011 | Ginisty | C12N 15/746 |
| | | | 435/69.1 |
| 2011/0189225 A1 * | 8/2011 | Turner et al. | 424/200.1 |
| 2011/0189236 A1 * | 8/2011 | Scott | C12N 15/746 |
| | | | 424/242.1 |
| 2012/0058096 A1 | 3/2012 | Vignali et al. | |
| 2012/0093870 A1 | 4/2012 | Boedeker et al. | |
| 2012/0100139 A1 | 4/2012 | Thompson et al. | |
| 2012/0189578 A1 | 7/2012 | Collison et al. | |
| 2013/0004547 A1 * | 1/2013 | Lam | A61K 39/145 |
| | | | 424/400 |
| 2013/0129723 A1 | 5/2013 | Blankenship et al. | |
| 2013/0164380 A1 | 6/2013 | Durum et al. | |
| 2013/0183326 A9 | 7/2013 | Vignali et al. | |
| 2015/0231228 A1 * | 8/2015 | Amara | A61K 39/21 |
| | | | 424/188.1 |
| 2015/0258201 A1 * | 9/2015 | Guerry | A61K 47/4833 |
| | | | 424/190.1 |
| 2015/0266932 A1 * | 9/2015 | Savarino | A61K 39/0258 |
| | | | 424/190.1 |
| 2015/0320850 A1 * | 11/2015 | Svennerholm | A61K 39/0258 |
| | | | 424/257.1 |

FOREIGN PATENT DOCUMENTS

| | | | |
|---|---|---|---|
| EP | 1084709 A1 | 3/2001 | |
| EP | 1543836 * | 6/2005 | A61K 39/108 |
| EP | 1947110 | 8/2013 | |
| EP | 2517724 | 11/2013 | |
| FR | 2947840 * | 1/2011 | C12N 15/67 |
| WO | WO9520657 | 8/1995 | |
| WO | 96/32487 * | 10/1996 | C12N 15/74 |
| WO | 01/02570 * | 1/2001 | C12N 15/16 |
| WO | 03/076643 * | 9/2003 | |
| WO | 2005/113827 * | 12/2005 | C12Q 1/68 |
| WO | 2007/089205 * | 8/2007 | A61K 39/106 |
| WO | 2008090223 A2 | 7/2008 | |
| WO | 2011/079282 * | 6/2011 | A01N 63/00 |
| WO | 2014047625 A1 | 3/2014 | |

OTHER PUBLICATIONS

102031262, Apr. 2011, cn, Derwent English Ab.*
Shaw, DM et al, Immunology, 2000, vol. 100, pp. 510-518, Engineering the microflora to vaccinate the mucosa:serum immunoglobulin G responses and activated draining cervical lymph nodes following mucoal application of tetanus toxin fragment C expressing lactobacilli.*
Pouwels, Peter H et al, Journal of Biotechnology, vol. 44, 1996, pp. 183-192, The potential of Lactobacillus as a carrier for oral immunization: Development and preliminary characterization of vector systems for targeted delivery of antigens.*
Borrero, Juan et al, Applied Microbiology and Biotechnology, vol. 89, 2011, pp. 131-143, Use of the usp45 lactococcal secretion signal sequence to drive the secretion and functional expression of enterococcal bacteriocins in Lactococcus lactis.*
Wei, Wenzhong et al, Biotechnology Letters, vol. 24, pp. 1669-1672, 2002, Two tandem promoters to increase gene expression in Lactococcus lactis.*
deVries, Maaike C. et al, Systemic and Applied Microbiology, vol. 29, 2006, pp. 358-367, Comparative and functional analysis of the rRNA-operons and their tRNA gene complement in different lactic acid bacteria.*
Rush, Catherine M., Lactobacilli:vehicles for antigen delivery to the female urogenital tract, Advances in Mucosal Immunology, edited by J. Mestecky, Plenum Press, New York, 1995, pp. 1547-1552.*
Wells, JM et al, Antonie van Leeuwenhoek, vol. 70, pp. 317-330, 1996, Lactic acid bacteria as vaccone delivery vehicles.*
Kochetkova, I., Trunkle, T., Callis, G., Pascual, D.W., 2008, Vaccination Without Autoantigen Protects Against Collagen II-Induced Arthritis via Immune Deviation and Regulatory T Cells, J. of Immunology, 181:2741-2452.
Scott, D.L., Wolfe, F., Huizinga, T.W., 2010, Rheumatoid arthritis, Lancet, 376(9746): 1094-1108.
Lozano, L.R., Naghavi, M., Foreman, K., Lim, S., Shibuya, K., Aboyans, V., Abraham, J., Adair, T. et al., 2012, Global and regional mortality from 235 causes of death for 20 age groups in 1990 and 2010: a systematic analysis for the Global Burden of Disease Study 2010, Lancet, 380 (9859):2095-2128.
Attridge, S.R., Davies, R., LaBrooy, J.T., 1997, Oral delivery of foreign antigens by attenuated *Salmonella*: consequences of prior exposure to the vector strain, Vaccine, 15(2):155-162.

(56) References Cited

OTHER PUBLICATIONS

Detmer, A., Glenting, J., 2006, Live bacterial vaccines—a review and identification of potential hazards, Microbial Cell Factories, 5:23, 1-12.

Sonomoto, K., Yokota, A., 2011, Lactic Acid Bacteria and Bifidobacteria: Current Progress in Advanced Research. Caister Academic Press. ISBN 978-1-904455-82-0.

Qadri, F., Svennerholm, A.M., Faruque, A.S., Sack, R.B., 2005, Enterotoxigenic *Escherichia coli* in developing countries: Epidemiology, microbiology, clinical features, treatment, and prevention, Clin Microbiol Rev, 18:465-483.

Low, D., Braaten, B., Van der Woude, M., 1996, Fimbriae in *Escherichia coli* and *Salmonella*: Cellular and Molecular Biology, eds. Neidhart F.C., et al., Am. Soc. Microbiol., Washington, D.C., vol. 2, pp. 146-157.

Soto, G.E., Hultgren, S.J., 1999, Bacterial adhesins: Common themes and variations in architecture and assembly, J Bacteriol, 181:1059-1071.

Wu, S., Pascual D.W., VanCott, J.L., McGhee, Jr., Maneval, D.R. Jr., Levine, M.M., and Hone, D.M., 1995, Immune responses to *Escherichia coli* and *Salmonella typhimurium* vectors that express colonization factor antigen I (CFA/I) of enterotoxigenic *E. coli* (ETEC) in the absence of the CFA/I positive regulator cfaR., Infect. Immun., 63:4933-4938.

Baker, K.K., Levine, M.M., Morison, J., Phillips, A., Barry, E.M., 2009, CfaE tip mutations in enterotoxigenic *Escherichia coli* CFA/I fimbriae define critical human intestinal binding sites, Cell Microbiology, 11(5):742-754.

Sakellaris, H., Balding, D.P., Scott, J.R., 1996, Assembly proteins of CS1 pili of enterotoxigenic *Escherichia coli*, Mol Microbiol., 21:529-541.

Courtenay, J. S., Dallman, M.J., Dayan, A.D., Martin, A., Mosedale, B., 1980, Immunization against heterologous type II collagen induces arthritis in mice, Nature, 283: 666-668.

Terato, K., Hasty, K.A., Reife, R.A., Cremer, M.A., Kang, A.H., Stuart, J.M., 1992, Induction of arthritis with monoclonal antibodies to collagen, J. Immunol., 148: 2103-2108.

Terato, K., Haeper, D.S., Griffiths, M.M., Hasty, D.L., Ye, X.J., Cremer, M.A., Seyer, J.M., 1995, Collagen-induced arthritis in mice: synergistic effect of *E. coli* lipopolysaccharide bypasses epitope specificity in the induction of arthritis with monoclonal antibodies to type II collagen, Autoimmun, 22: 137-147.

Constantinescu, C.S., Farooqi, N., O'Brien, K., Gran, B., 2011, Experimental autoimmune encephalomyelitis (EAE) as a model for multiple sclerosis (MS), Br J Pharmacol., 164(4):1079-106.

Madsen, S.M., Arnau, J., Vrang, A., Givskov, M., and Israelsen, H., 1999, Molecular characterization of the pH-inducible and growth phase-dependent promoter P170 of Lactococcus lactis., Mol. Microbiol., 32:75-87.

Jensen, P.R. and Hammer, K., 1998, The sequence of spacers between the consensus sequences modulates the strength of prokaryotic promoters, Appl. Environ. Microbiol., 64:82-87.

Narita, J., Ishida, S., Okano, K., Kimura, S., Fukuda, H., and Kondo, A., 2006, Improvement of protein production in lactic acid bacteria using 5'-untranslated leader sequence of slpA from Lactobacillus acidophilus, Improvement in protein production using UTLS, Appl. Microbiol. Biotechnol., 73:366-373.

Lee, P. and Faubert, G.M., 2006, Oral immunization of BALB/c mice by intragastric delivery of *Streptococcus gordonii*-expressing Giardia cyst wall protein 2 decreases cyst shedding in challenged mice, FEMS Microbiol. Lett., 265:225-236.

Steen, A., Buist, G., Kramer, N.E., Jalving, R., Benus, G.F., Venema, G., Kuipers, O.P, and Kok, J., 2008, Reduced lysis upon growth of Lactococcus lactis on galactose is a consequence of decreased binding of the autolysin AcmA, Appl. Environ. Microbiol., 74:4671-4679.

Oddone, G.M., Mills, D.A., and Block, D.E., 2009, Incorporation of nisI-mediated nisin immunity improves vector-based nisin-controlled gene expression in lactic acid bacteria, Plasmid, 61:151-158.

Jun, S., Gilmore, W., Callis, G., Rynda, A., Haddad, A., and Pascual, D.W., 2005, A live diarrheal vaccine imprints a Th2 cell bias and acts as an anti-inflammatory vaccine, J. Immunol., 175:6733-6740.

Ochoa-Repáraz, J., Riccardi, C., Rynda, A., Jun, S., Callis, G., and Pascual, D.W., 2007, Regulatory T cell vaccination without autoantigen protects against experimental autoimmune encephalomyelitis, J. Immunol., 178:1791-1799.

Ochoa-Repáraz, J., Rynda, A., Ascón, M.A., Yang, X., Kochetkova, I., Riccardi, C., Callis, G., Trunkle, T., and Pascual, D.W., 2008, IL-13 production by regulatory T cells protects against experimental autoimmune encephalomyelitis independently of autoantigen, J. Immunol., 181:954-968.

Pascual et al. "Expression of recombinant enterotoxigenic *Escherichia coli* colonization factor antigen I by *Salmonella typhimurium* elicits a biphasic T helper cell response" Infection and Immunity 67; 6249 (1999).

Pascual et al. "Tolerance in the absence of autoantigen" Endocr Metab Immune Disord Drug Targets 7; 203 (2007).

Kochetkova et al. IL-35 stimulation of CD39+ regulatory T cells confers protection against collagen II-induced arthritis via the production of IL-10. J Immunol 15; 184 (2010).

Kochetkova et al. "Colonization factor antigen I expression by *Salmonella* induces CREB-dependent stimulation of CD39+ CD4+ T cells responsible for protection against collagen-induced arthritis" Journal of Immunology 186, 107.5 (2011).

Jun et al. "Bystander-mediated stimulation of proteolipid protein-specific regulatory T (Treg) cells confers protection against experimental autoimmune encephalomyelitis (EAE) via TGF-beta" Journal of Neuroimmunology 245; 39 (2012).

Pascual et al. "Attenuating gene expression (AGE) for vaccine development" Virulence 4:5 385 (2013).

Evans et al. "Purification and Characterization of the CFA/I Antigen of Enterotoxigenic *Escherichia coli*" Infection and Immunity, Aug. 1979, p. 738-748.

Evans et al. "Administration of purified colonization factor antigens (CFA/I, CFA/II) of enterotoxigenic *Escherichia coli* to volunteers. Response to challenge with virulent enterotoxigenic *Escherichia coli*" Gastroenterology Oct. 1984;87(4):934-40.

de la Cabada "Immunoprotection against enterotoxigenic *Escherichia coli* diarrhea in rabbits by peroral administration of purified colonization factor antigen I (CFA/I)" FEMS Microbiology Letters vol. 11, issue 4 303-307, 1981.

Kocketkova et al., 2013 "*E. coli* fimbriae serve as an IL-35 agonist stimulating indoleamine 2,3 dioxygenase for protection against collagen-induced arthritis (P5154)" The Journal of Immunology 190,195.6 (Abstract).

Kocketkova et al., 2012 "IL-35 essential for protection against collagen-induced arthritis (CIA) following intervention wiht *Escherichia coli* colonization antigen I (CFA/I) fimbrae" The Journal of Immunology 188, 116.2 (Abstract).

Li et al., 2012 "IL-35 is a Novel Responsive Anti-inflammatory Cytokine—A New System of Categorizing Anti-inflammatory Cytokines". PLoS One 7(3) e33628.

Bai et al., 2012 "Erythromycin Enhances CD4+Foxp3+ Regulatory T-Cell Responses in a Rat Model of Smoke-Induced Lung Inflammation" Mediators of Inflammation vol. 2012 ID 410232.

Niedbala et al., 2007 "IL-35 is a novel cytokine with therapeutic effects against collagen-induced arthritis through the expansion of regulatory T cells and suppression of Th17 cells" Eur. J. Immunol. 37:3021-3029.

With et al., 2011 "Interleukin-35 Mediates Mucosal Immune Responses That Protect Against T-Cell-Dependent Colitis" Gastroenterology Nov 141(5):1875-1886.

Bettini et al., 2012 "Prevention of Autoimmune Diabetes by Ectopic Pancreatic B-Cell Expression of Interleukin-35" Diabetes 61:1519-1526.

Sambrook and Russell (2001) Molecular Cloning: A Laboratory Manual (3rd edition), Cold Spring Harbor Laboratory, Cold Spring Harbor Laboratory Press, New York.

Alfonso R. Gennaro. Remington: The Science and Practice of Pharmacy, 20th Edition. Baltimore, MD: Lippincott Williams & Wilkins, 2000.

EPO Communication Pursuant to Rules 161(1) and 162 EPC for EP13771738.5; mailed on May 6, 2015.

Written Opinion of International Search Report for PCT/US2013/061393; mailed on Mar. 24, 2015.

International Search Report for PCT/US2013/061393; mailed on Jan. 14, 2014.

International Preliminary Report on Patentability for PCT/US2013/061393; mailed on Mar. 24, 2015.

\* cited by examiner

SEQUENCE LISTING

<160> NUMBER OF SEQ ID NOS: 12

<210> SEQ ID NO 1
<211> LENGTH: 5565
<212> TYPE: DNA
<213> ORGANISM: Artificial Sequence
<220> FEATURE:
<223> OTHER INFORMATION: Engineered CFA/I Operon

<400> SEQUENCE: 1

```
tctagaagtc ttataactat actgacaata gaaacattaa caaatctaaa acagtcttaa      60
ttctatcttg agaaagtatt ggtaataata ttattgtcga taacgcgagc ataataaacg     120
gctctgatta aattctgaag tttgttagat acaatgattt cgttcgaagg aactacaaaa     180
taaattattc tagaccaggt gatatcaata tgcgaaaaga actatgaata tccactccat     240
ttttggttgc catttgttaa cgctgcctcc tctccctagt gctataataa aacaggccca     300
ttttggaaca gacttctact attttgttgt agatctgggc cccatttggc agtttattct     360
tgacatgtag tgaggggggct ggtataatca catagtactg tttgattctt cagcaagact     420
ggtacctcat gagagttata gactcatgga tcttgctttg aagggttttg tacattatag     480
gctcctatca catgctgaac ctatggccta ttacatttt ttatatttca aggaggaccg     540
gtaccaggta ctagtgtcgc gaggagggct agttctagaa tgaaaaaaaa gattatctca     600
gctattttaa tgtctacagt gatactttct gctgcagccc cgttgtcagg tgtttacgct     660
gctagcgaga aaaatattac tgtaacagct agtgttgatc ctgcaattga tcttttgcaa     720
gctgatggca atgctctgcc atcagctgta aagttagctt attctcccgc atcaaaaact     780
tttgaaagtt acagagtaat gactcaagta catacaaacg atgcaactaa aaaagtaatt     840
gttaaacttg ctgatacacc acagcttaca gatgttctga attcaactgt tcaaatgcct     900
atcagtgtgt catgggagg acaagtatta tctacaacag ccaaagaatt tgaagctgct     960
gctttgggat attctgcatc cggtgtaaat ggcgtatcat cttctcaaga gttagtaatt    1020
agcgctgcac ctaaaactgc cggtaccgcc ccaactgcag gaaactattc aggagtagta    1080
tctcttgtaa tgactttggg atcctgaggg cccaggaggg tttaaacatg aaaaagatta    1140
atctggcatt attgaccctc gcaactttga tgggtgtttc ttcaacagct gttgtatttg    1200
```

```
ccggcaactt tatgatatat ccaatatcaa aagatttaaa gaatggaaat agcgagttag    1260
ttcgtgttta ttcaaaatca aaagagatac aatatataaa aatatataca aagaagatta    1320
ttaatcccgg tacaactgaa gaatataagg ttgatatacc caattgggat ggtgggcttg    1380
tagtcactcc tcagaaagtt atcctccctg caggagcgag taaatcaata cgtttaactc    1440
aatttaaaat accaaaaaaa gaggaagttt acagagtata ttttgaggcg gtaaaaccag    1500
atagcaaaga aaatgtaatt gataataaaa aactaacaac agagctatct gttaatataa    1560
tttatgcggc tctaattaga tctttaccaa gtgaacaaaa tatatcacta aatatttcta    1620
gaaatgcaaa aaaaaatata attatttata ataatgggaa tgttagagca ggcgttaaag    1680
atatttattt ttgtaagtca tctaatatcg atgataactg tgtaaaaaaa gcgtataaca    1740
agaatatata tccagaaaaa gtcatttgag ccggctcgcg aatgaaaaag attttgatca    1800
ctacgacatt agcacttgct ctcctgtctt taggtgcagc tagcgttacc ggagatatac    1860
ccgactcttt ccgtgattta tggggagaac aagatgaatt ttatgaagta aaactatatg    1920
ggcaaactct aggaatacat cgaattaaaa caaccccaac acatattaag ttttattcac    1980
ccgaaagcat tttagataaa ataaatttaa aaaagaaaa ggaaaaggaa ttgagtgttt    2040
tttttactaa ttcttttttca agaaatggca atatgagttg tcagggtaac actactatac    2100
agtataactg caattacatt aaaacaaaat cagtagatgt catcgttgat gatgttgata    2160
atgttgttaa ccttttttata ggtaatgaat ttctggattc tgaagcacac aatgatgaat    2220
atcatcaatt atcacggaat gtaaaaaaag cttttataca aagccagaca attaatctct    2280
cagattctgg aaagtataaa agattgtcta tttcagggaa tagcgcgctg ggtattacag    2340
atacaagtta tgctgtctta aattggtgga tgaattacaa taaatctaat ggttacagca    2400
acaacgaaaa aacaatcaat agtttatact ttagacatga tttagataag agatattatt    2460
atcaatttgg acgaatggat cgtacagatt tatcacaaag tattagcggg agctttaatt    2520
ttaacttact tcctttaccc gatattgatg gtatacggac aggaaccaca caatcttata    2580
tcaaaaatac agataagttt atcgcatccc ctgtaactgt tatgttaact aattttttcca    2640 gagtggaagc ttttcgcaat gatcaattat tgggcgtatg gtatttagat tctggagtaa    2700
atgaattaga tacagctcgt ttaccttatg gcagttacga tcttaaatta aaaattttttg    2760 aaaacactca attagttcgt gaagaaataa ttcctttttaa taaggaaga agctctattg    2820 gtgatatgca atgggatatt ttcgttcagg gagggaatat tgttaatgat aatgatcgtt    2880
acatagaaaa acaaaataat cataagtcat cgattaatac tgggctacgt ttaccaatta    2940
cgaaaaatat ctctgttcaa cagggagtat ctgttataga taataaaagt tattatgaag    3000
gaagtctgaa atggaattcc ggcattctat ctggctcact aaatagtgag ttcagttttc    3060
tttggggaga taatgcaaaa ggtaattatc aaagtatctc gtataccgat ggatttagct    3120
tatcatttta tcataatgat aagcgggtcg ataattgtgg aagaaattac aatgctggtt    3180
ggagtggatg ctacgaatca tattcggcat ctttaagtat tcctttatta ggatggacaa    3240
gtactctggg atatagtgac acttatagtg aatcagtgta taaaagccat attctttctg    3300
aatatggctt ttataatcaa aacatatata aagggagaac ccaaagatgg caactgactt    3360
catccacctc tttaaaatgg atggattata attttatgcc agcaattgga atatataaca    3420
gtgaacaaag acaactgact gataaaggcg gatatatatc tgtaactatc acccgagcca    3480
gcagagaaaa ttcattaaat acagggtatt cttacaacta ttccagagga aactattctt    3540
ctaacgaatt attttgttgat ggatatatga catcaacaaa taatggtgat tatcatgagg    3600
```

-continued

```
caggaatgcg ttttaataaa aatagacata atgcagaagg tagactttca ggtcgtataa    3660
acaatcgatt tggagattta atggttcat tcagcatgaa taaaaacaga aacaccaaca     3720
gtaccaatca ttctctcact ggtggttata attcctcatt tgctcttaca agtgatggat    3780
tttactgggg aggaagtaca gctggtttga caaaactggc tggcggtatt atcaaggtta    3840
aatcaaacga tactaaaaaa aacttggtaa aagtgactgg gacattgtac ggtgattatt    3900
cgctagggag caacgataat gcttttattc ctgtaccagc attaactcca gccagtttaa    3960
tcattgaaga taataattat ggtgataata atatttctat acttgcgcca acaaacaacg    4020
atatgtttat gttgccgggt aatgtttatc ctgttgaaat tgaaaccaaa gtaagtgttt    4080
cttatattgg tagaggtttt gacccaaacg gcacgccact ttctggcgca catgttttga    4140
atgaaccaca tgttatcctg gatgaggacg gtggattttc gtttgaatat acaggtaatg    4200
agaaaacact ttttttatta aagggcagga ctatttatac atgtcaactg gggaaaaata    4260
aagttcataa aggcattgtt ttcgtcgggg atgttatatg tgatattaat agcacaagtt    4320
ccttaccaga tgaatttgta agaacccac gtgtgcagga tttgctggca agaatgata     4380 aaggataaac ggctagcgtt taaaccgact cagtggtcga catgcaaagg aaaaagaaag    4440
ggctatcgtt cttgttagcc ggtacagtcg ctttaggggc gctggctgtc ttgccagtcg    4500
gcgaaatcca agcaaaggcg gccgcagata aaaatcccgg aagtgaaaac atgactaata    4560
ctattggtcc ccatgacagg gggggatctt cccccatata taatatctta aattcctatc    4620
ttacagcata caatgaagc catcatctgt atgataggat gagttttta tgtttgtctt      4680 ctcaaaatac actgaatgga gcatgcccaa gcagtgatgc ccctggcact gctacaattg    4740
atggcgaaac aaatataaca ttacaattta cggaaaaaag aagtctaatt aaaagagaac    4800
tgcaaattaa aggctataaa caattttttgt tcaaaaatgc taattgccca tctaaactag    4860
cacttaactc atctcatttt caatgtaata gagaacaagc ttcaggtgct actttatcgt    4920
tatacatacc agctggtgaa ttaaataaat taccttttgg ggggtctgg aatgccgttc     4980 tgaagctaaa tgtaaaaaga cgatatgata caacctatgg gacttacact ataaacatca    5040
cagttaattt aactgataag ggaaatattc agatatggtt accacagttc aaaagtaacg    5100
ctcgtgtcga tcttaacttg cgtccaactg gtggtggtac atatatcgga agaaattctg    5160
ttgatatgtg ctttatgat ggatatagta ctaacagcag ctctttggag ataagatttc     5220
aggatgataa ttctaaatct gatggaaaat tttatctaaa gaaataaat gatgactcca     5280 aagaacttgt atacactttg tcacttctcc tggcaggtaa aaatttaaca ccaacaaatg    5340
gacaggcatt aaatattaac actgcttctc tggaaacaaa ctggaataga attcagctg     5400 tcaccatgcc agaaatcagt gttccggtgt tgtgttggcc tggacgtttg caattggatg    5460
caaaagtgaa aaatcccgag gctggacaat atatggggaa tattaaaatt actttcacac    5520
caagtagtca aacactctag tctagactcg agaccaggta ccggt                    5565
```

<210> SEQ ID NO 2
<211> LENGTH: 528
<212> TYPE: DNA
<213> ORGANISM: Artificial Sequence
<220> FEATURE:
<223> OTHER INFORMATION: Engineered E. coli cfaB gene with Lactococcus
      signal sequence

<400> SEQUENCE: 2

```
atgaaaaaaa agattatctc agctatttta atgtctacag tgatactttc tgctgcagcc    60
```

```
ccgttgtcag gtgtttacgc tgctagcgag aaaaatatta ctgtaacagc tagtgttgat    120
cctgcaattg atcttttgca agctgatggc aatgctctgc catcagctgt aaagttagct    180
tattctcccg catcaaaaac ttttgaaagt tacagagtaa tgactcaagt acatacaaac    240
gatgcaacta aaaagtaat tgttaaactt gctgatacac cacagcttac agatgttctg     300
aattcaactg ttcaaatgcc tatcagtgtg tcatggggag gacaagtatt atctacaaca    360
gccaaagaat tgaagctgc tgctttggga tattctgcat ccggtgtaaa tggcgtatca     420
tcttctcaag agttagtaat tagcgctgca cctaaaactg ccggtaccgc cccaactgca    480
ggaaactatt caggagtagt atctcttgta atgactttgg gatcctga                528

<210> SEQ ID NO 3
<211> LENGTH: 642
<212> TYPE: DNA
<213> ORGANISM: artificial
<220> FEATURE:
<223> OTHER INFORMATION: Engineered E. coli cfaA gene with Lactococcus
      signal sequence

<400> SEQUENCE: 3
atgaaaaaga ttaatctggc attattgacc ctcgcaactt tgatgggtgt ttcttcaaca     60
gctgttgtat ttgccggcaa ctttatgata tatccaatat caaaagattt aaagaatgga    120
aatagcgagt tagttcgtgt ttattcaaaa tcaaaagaga tacaatatat aaaaatatat    180
acaaagaaga ttattaatcc cggtacaact gaagaatata aggttgatat acccaattgg    240
gatggtgggc ttgtagtcac tcctcagaaa gttatcctcc ctgcaggagc gagtaaatca    300
atacgtttaa ctcaatttaa ataccaaaa aagaggaag tttacagagt atattttgag      360
gcggtaaaac cagatagcaa agaaaatgta attgataata aaaaactaac aacagagcta    420
tctgttaata taatttatgc ggctctaatt agatctttac caagtgaaca aaatatatca    480
ctaaatattt ctagaaatgc aaaaaaaaat ataattattt ataataatgg gaatgttaga    540
gcaggcgtta agatatttta ttttgtaag tcatctaata tcgatgataa ctgtgtaaaa     600
aaagcgtata acaagaatat atatccagaa aaagtcattt ga                      642

<210> SEQ ID NO 4
<211> LENGTH: 2607
<212> TYPE: DNA
<213> ORGANISM: artificial
<220> FEATURE:
<223> OTHER INFORMATION: Engineered E. coli cfaC gene with Lactococcus
      signal sequence

<400> SEQUENCE: 4
atgaaaaaga ttttgatcac tacgacatta gcacttgctc tcctgtcttt aggtgcagct     60
agcgttaccg gagatatacc cgactctttc cgtgatttat ggggagaaca agatgaattt    120
tatgaagtaa actatatgg gcaaactcta ggaatacatc gaattaaaac aaccccaaca    180
catattaagt tttattcacc cgaaagcatt ttagataaaa taaatttaaa aaaagaaaag    240
gaaaaggaat tgagtgtttt ttttactaat tcttttttcaa gaaatggcaa tatgagttgt    300
cagggtaaca ctactataca gtaaactgc aattacatta aacaaaatc agtagatgtc    360 atcgttgatg atgttgataa tgttgttaac ctttttatag gtaatgaatt tctggattct    420
gaagcacaca atgatgaata tcatcaatta tcacggaatg taaaaaagc ttttatacaa    480 agccagacaa ttaatctctc agattctgga agtataaaa gattgtctat ttcagggaat    540
```

```
agcgcgctgg gtattacaga tacaagttat gctgtcttaa attggtggat gaattacaat        600
aaatctaatg gttacagcaa caacgaaaaa acaatcaata gtttatactt tagacatgat        660
ttagataaga gatattatta tcaatttgga cgaatggatc gtacagattt atcacaaagt        720
attagcggga gctttaattt taacttactt cctttacccg atattgatgg tatacggaca        780
ggaaccacac aatcttatat caaaaataca gataagttta tcgcatcccc tgtaactgtt        840
atgttaacta ttttttccag agtggaagct tttcgcaatg atcaattatt gggcgtatgg        900
tatttagatt ctggagtaaa tgaattagat acagctcgtt taccttatgg cagttacgat        960
cttaaattaa aaattttga aaacactcaa ttagttcgtg aagaaataat tccttttaat       1020
aaaggaagaa gctctattgg tgatatgcaa tgggatattt tcgttcaggg agggaatatt       1080
gttaatgata tgatcgttac catagaaaaa caaataatc ataagtcatc gattaatact       1140
gggctacgtt taccaattac gaaaaatatc tctgttcaac agggagtatc tgttatagat       1200
aataaaagtt attatgaagg aagtctgaaa tggaattccg gcattctatc tggctcacta       1260
aatagtgagt tcagttttct ttggggagat aatgcaaaag gtaattatca aagtatctcg       1320
tataccgatg gatttagctt atcattttat cataatgata agcgggtcga taattgtgga       1380
agaaattaca atgctggttg gagtggatgc tacgaatcat attcggcatc tttaagtatt       1440
cctttattag gatggacaag tactctggga tatagtgaca cttatagtga atcagtgtat       1500
aaaagccata ttctttctga atatggcttt tataatcaaa acatatataa agggagaacc       1560
caaagatggc aactgacttc atccacctct ttaaaatgga tggattataa ttttatgcca       1620
gcaattggaa tatataacag tgaacaaaga caactgactg ataaaggcgg atatatatct       1680
gtaactatca cccgagccag cagagaaaat tcattaaata cagggtattc ttacaactat       1740
tccagaggaa actattcttc taacgaatta tttgttgatg gatatatgac atcaacaaat       1800
aatggtgatt atcatgaggc aggaatgcgt tttaataaaa atagacataa tgcagaaggt       1860
agactttcag gtcgtataaa caatcgattt ggagatttaa atggttcatt cagcatgaat       1920
aaaaacagaa acaccaacag taccaatcat tctctcactg gtggttataa ttcctcattt       1980
gctcttacaa gtgatggatt ttactgggga ggaagtacag ctggtttgac aaaactggct       2040
ggcggtatta tcaaggttaa atcaaacgat actaaaaaa acttggtaaa agtgactggg       2100
acattgtacg gtgattattc gctagggagc aacgataatg ctttttattcc tgtaccagca       2160 ttaactccag ccagtttaat cattgaagat aataattatg gtgataataa tatttctata       2220
cttgcgccaa caaacaacga tatgtttatg ttgccgggta atgtttatcc tgttgaaatt       2280
gaaaccaaag taagtgtttc ttatattggt agaggttttg acccaaacgg cacgccactt       2340
tctggcgcac atgttttgaa tgaaccacat gttatcctgg atgaggacgg tggattttcg       2400
tttgaatata caggtaatga gaaaacactt tttttattaa agggcaggac tatttataca       2460
tgtcaactgg ggaaaaataa agttcataaa ggcattgttt tcgtcgggga tgttatatgt       2520
gatattaata gcacaagttc cttaccagat gaatttgtaa agaacccacg tgtgcaggat       2580
ttgctggcaa agaatgataa aggataa                                          2607
```

<210> SEQ ID NO 5  
<211> LENGTH: 1119  
<212> TYPE: DNA  
<213> ORGANISM: artificial  
<220> FEATURE:  
<223> OTHER INFORMATION: Engineered E. coli cfaE gene with Lactococcus signal sequence

<400> SEQUENCE: 5

```
atgcaaagga aaaagaaagg gctatcgttc ttgttagccg gtacagtcgc tttaggggcg        60
ctggctgtct tgccagtcgg cgaaatccaa gcaaaggcgg ccgcagataa aaatcccgga       120
agtgaaaaca tgactaatac tattggtccc catgacaggg ggggatcttc ccccatatat       180
aatatcttaa attcctatct tacagcatac aatggaagcc atcatctgta tgataggatg       240
agttttttat gtttgtcttc tcaaaataca ctgaatggag catgcccaag cagtgatgcc       300
cctggcactg ctacaattga tggcgaaaca aatataacat acaatttac ggaaaaaga        360
agtctaatta aaagagaact gcaaattaaa ggctataaac aattttttgtt caaaaatgct       420
aattgcccat ctaaactagc acttaactca tctcattttc aatgtaatag agaacaagct       480
tcaggtgcta ctttatcgtt atacatacca gctggtgaat taaataaatt acctttggg        540
ggggtctgga atgccgttct gaagctaaat gtaaaaagac gatatgatac aacctatggg       600
acttacacta taaacatcac agttaattta actgataagg gaaatattca gatatggtta       660
ccacagttca aaagtaacgc tcgtgtcgat cttaacttgc gtccaactgg tggtggtaca       720
tatatcggaa gaaattctgt tgatatgtgc ttttatgatg gatatagtac taacagcagc       780
tctttggaga taagatttca ggatgataat tctaaatctg atggaaaatt ttatctaaag       840
aaaataaatg atgactccaa agaacttgta tacactttgt cacttctcct ggcaggtaaa       900
aatttaacac caacaaatgg acaggcatta aatattaaca ctgcttctct ggaaacaaac       960
tggaatagaa ttacagctgt caccatgcca gaaatcagtg ttccggtgtt gtgttggcct      1020
ggacgtttgc aattggatgc aaaagtgaaa atcccgagg ctggacaata tgggggaat       1080
attaaaatta ctttcacacc aagtagtcaa acactctag                             1119
```

<210> SEQ ID NO 6
<211> LENGTH: 187
<212> TYPE: DNA
<213> ORGANISM: Lactococcus lactis

<400> SEQUENCE: 6

```
agtcttataa ctatactgac aatagaaaca ttaacaaatc taaaacagtc ttaattctat        60
cttgagaaag tattggtaat aatattattg tcgataacgc gagcataata aacggctctg       120
attaaattct gaagtttgtt agatacaatg atttcgttcg aaggaactac aaaataaatt       180
attctag                                                                 187
```

<210> SEQ ID NO 7
<211> LENGTH: 142
<212> TYPE: DNA
<213> ORGANISM: Lactococcus lactis

<400> SEQUENCE: 7

```
gatatcaata tgcgaaaaga actatgaata tccactccat ttttggttgc catttgttaa        60
cgctgcctcc tctccctagt gctataataa acaggccca ttttggaaca gacttctact       120
attttgttgt agatctgggc cc                                                142
```

<210> SEQ ID NO 8
<211> LENGTH: 194
<212> TYPE: DNA
<213> ORGANISM: Lactococcus lactis

<400> SEQUENCE: 8

```
catttggcag tttattcttg acatgtagtg aggggggctgg tataatcaca tagtactgtt        60
```

```
tgattcttca gcaagactgg tacctcatga gagttataga ctcatggatc ttgctttgaa    120
gggttttgta cattataggc tcctatcaca tgctgaacct atggcctatt acatttttt    180 atatttcaag gagg                                                      194
```

<210> SEQ ID NO 9
<211> LENGTH: 175
<212> TYPE: PRT
<213> ORGANISM: Artificial Sequence
<220> FEATURE:
<223> OTHER INFORMATION: Engineered E. coli CfaB peptide with
      Lactococcus signal peptide

<400> SEQUENCE: 9

```
Met Lys Lys Lys Ile Ile Ser Ala Ile Leu Met Ser Thr Val Ile Leu
1               5                   10                  15

Ser Ala Ala Ala Pro Leu Ser Gly Val Tyr Ala Ala Ser Glu Lys Asn
            20                  25                  30

Ile Thr Val Thr Ala Ser Val Asp Pro Ala Ile Asp Leu Leu Gln Ala
        35                  40                  45

Asp Gly Asn Ala Leu Pro Ser Ala Val Lys Leu Ala Tyr Ser Pro Ala
    50                  55                  60

Ser Lys Thr Phe Glu Ser Tyr Arg Val Met Thr Gln Val His Thr Asn
65                  70                  75                  80

Asp Ala Thr Lys Lys Val Ile Val Lys Leu Ala Asp Thr Pro Gln Leu
                85                  90                  95

Thr Asp Val Leu Asn Ser Thr Val Gln Met Pro Ile Ser Val Ser Trp
            100                 105                 110

Gly Gly Gln Val Leu Ser Thr Thr Ala Lys Glu Phe Glu Ala Ala Ala
        115                 120                 125

Leu Gly Tyr Ser Ala Ser Gly Val Asn Gly Val Ser Ser Ser Gln Glu
    130                 135                 140

Leu Val Ile Ser Ala Ala Pro Lys Thr Ala Gly Thr Ala Pro Thr Ala
145                 150                 155                 160

Gly Asn Tyr Ser Gly Val Val Ser Leu Val Met Thr Leu Gly Ser
                165                 170                 175
```

<210> SEQ ID NO 10
<211> LENGTH: 213
<212> TYPE: PRT
<213> ORGANISM: Artificial Sequence
<220> FEATURE:
<223> OTHER INFORMATION: Engineered E. coli CfaA peptide with
      Lactococcus signal peptide

<400> SEQUENCE: 10

```
Met Lys Lys Ile Asn Leu Ala Leu Leu Thr Leu Ala Thr Leu Met Gly
1               5                   10                  15

Val Ser Ser Thr Ala Val Val Phe Ala Gly Asn Phe Met Ile Tyr Pro
            20                  25                  30

Ile Ser Lys Asp Leu Lys Asn Gly Asn Ser Glu Leu Val Arg Val Tyr
        35                  40                  45

Ser Lys Ser Lys Glu Ile Gln Tyr Ile Lys Ile Tyr Thr Lys Lys Ile
    50                  55                  60

Ile Asn Pro Gly Thr Thr Glu Glu Tyr Lys Val Asp Ile Pro Asn Trp
65                  70                  75                  80

Asp Gly Gly Leu Val Val Thr Pro Gln Lys Val Ile Leu Pro Ala Gly
                85                  90                  95
```

```
Ala Ser Lys Ser Ile Arg Leu Thr Gln Phe Lys Ile Pro Lys Lys Glu
            100                 105                 110

Glu Val Tyr Arg Val Tyr Phe Glu Ala Val Lys Pro Asp Ser Lys Glu
            115                 120                 125

Asn Val Ile Asp Asn Lys Lys Leu Thr Thr Glu Leu Ser Val Asn Ile
130                 135                 140

Ile Tyr Ala Ala Leu Ile Arg Ser Leu Pro Ser Glu Gln Asn Ile Ser
145                 150                 155                 160

Leu Asn Ile Ser Arg Asn Ala Lys Lys Asn Ile Ile Tyr Asn Asn
                165                 170                 175

Gly Asn Val Arg Ala Gly Val Lys Asp Ile Tyr Phe Cys Lys Ser Ser
            180                 185                 190

Asn Ile Asp Asp Asn Cys Val Lys Ala Tyr Asn Lys Asn Ile Tyr
            195                 200                 205

Pro Glu Lys Val Ile
            210
```

<210> SEQ ID NO 11
<211> LENGTH: 868
<212> TYPE: PRT
<213> ORGANISM: Artificial Sequence
<220> FEATURE:
<223> OTHER INFORMATION: Engineered E. coli CfaC peptide with
      Lactococcus signal peptide

<400> SEQUENCE: 11

```
Met Lys Lys Ile Leu Ile Thr Thr Thr Leu Ala Leu Ala Leu Leu Ser
1               5                   10                  15

Leu Gly Ala Ala Ser Val Thr Gly Asp Ile Pro Asp Ser Phe Arg Asp
            20                  25                  30

Leu Trp Gly Glu Gln Asp Glu Phe Tyr Glu Val Lys Leu Tyr Gly Gln
        35                  40                  45

Thr Leu Gly Ile His Arg Ile Lys Thr Thr Pro Thr His Ile Lys Phe
    50                  55                  60

Tyr Ser Pro Glu Ser Ile Leu Asp Lys Ile Asn Leu Lys Lys Glu Lys
65                  70                  75                  80

Glu Lys Glu Leu Ser Val Phe Phe Thr Asn Ser Phe Ser Arg Asn Gly
                85                  90                  95

Asn Met Ser Cys Gln Gly Asn Thr Thr Ile Gln Tyr Asn Cys Asn Tyr
            100                 105                 110

Ile Lys Thr Lys Ser Val Asp Val Ile Asp Asp Val Asp Asn Val
            115                 120                 125

Val Asn Leu Phe Ile Gly Asn Glu Phe Leu Asp Ser Glu Ala His Asn
130                 135                 140

Asp Glu Tyr His Gln Leu Ser Arg Asn Val Lys Lys Ala Phe Ile Gln
145                 150                 155                 160

Ser Gln Thr Ile Asn Leu Ser Asp Ser Gly Lys Tyr Lys Arg Leu Ser
                165                 170                 175

Ile Ser Gly Asn Ser Ala Leu Gly Ile Thr Asp Thr Ser Tyr Ala Val
            180                 185                 190

Leu Asn Trp Trp Met Asn Tyr Lys Ser Asn Gly Tyr Ser Asn Asn
            195                 200                 205

Glu Lys Thr Ile Asn Ser Leu Tyr Phe Arg His Asp Leu Asp Lys Arg
210                 215                 220

Tyr Tyr Tyr Gln Phe Gly Arg Met Asp Arg Thr Asp Leu Ser Gln Ser
```

```
            225                 230                 235                 240
        Ile Ser Gly Ser Phe Asn Phe Asn Leu Leu Pro Leu Pro Asp Ile Asp
                        245                 250                 255

Gly Ile Arg Thr Gly Thr Thr Gln Ser Tyr Ile Lys Asn Thr Asp Lys
                        260                 265                 270

Phe Ile Ala Ser Pro Val Thr Val Met Leu Thr Asn Phe Ser Arg Val
                        275                 280                 285

Glu Ala Phe Arg Asn Asp Gln Leu Leu Gly Val Trp Tyr Leu Asp Ser
            290                 295                 300

Gly Val Asn Glu Leu Asp Thr Ala Arg Leu Pro Tyr Gly Ser Tyr Asp
        305                 310                 315                 320

Leu Lys Leu Lys Ile Phe Glu Asn Thr Gln Leu Val Arg Glu Glu Ile
                        325                 330                 335

Ile Pro Phe Asn Lys Gly Arg Ser Ser Ile Gly Asp Met Gln Trp Asp
                        340                 345                 350

Ile Phe Val Gln Gly Gly Asn Ile Val Asn Asp Asn Asp Arg Tyr Ile
                        355                 360                 365

Glu Lys Gln Asn Asn His Lys Ser Ser Ile Asn Thr Gly Leu Arg Leu
            370                 375                 380

Pro Ile Thr Lys Asn Ile Ser Val Gln Gln Gly Val Ser Val Ile Asp
        385                 390                 395                 400

Asn Lys Ser Tyr Tyr Glu Gly Ser Leu Lys Trp Asn Ser Gly Ile Leu
                        405                 410                 415

Ser Gly Ser Leu Asn Ser Glu Phe Ser Phe Leu Trp Gly Asp Asn Ala
                        420                 425                 430

Lys Gly Asn Tyr Gln Ser Ile Ser Tyr Thr Asp Gly Phe Ser Leu Ser
                        435                 440                 445

Phe Tyr His Asn Asp Lys Arg Val Asp Asn Cys Gly Arg Asn Tyr Asn
                        450                 455                 460

Ala Gly Trp Ser Gly Cys Tyr Glu Ser Tyr Ser Ala Ser Leu Ser Ile
        465                 470                 475                 480

Pro Leu Leu Gly Trp Thr Ser Thr Leu Gly Tyr Ser Asp Thr Tyr Ser
                        485                 490                 495

Glu Ser Val Tyr Lys Ser His Ile Leu Ser Glu Tyr Gly Phe Tyr Asn
                        500                 505                 510

Gln Asn Ile Tyr Lys Gly Arg Thr Gln Arg Trp Gln Leu Thr Ser Ser
                        515                 520                 525

Thr Ser Leu Lys Trp Met Asp Tyr Asn Phe Met Pro Ala Ile Gly Ile
                        530                 535                 540

Tyr Asn Ser Glu Gln Arg Gln Leu Thr Asp Lys Gly Gly Tyr Ile Ser
        545                 550                 555                 560

Val Thr Ile Thr Arg Ala Ser Arg Glu Asn Ser Leu Asn Thr Gly Tyr
                        565                 570                 575

Ser Tyr Asn Tyr Ser Arg Gly Asn Tyr Ser Ser Asn Glu Leu Phe Val
                        580                 585                 590

Asp Gly Tyr Met Thr Ser Thr Asn Asn Gly Asp Tyr His Glu Ala Gly
                        595                 600                 605

Met Arg Phe Asn Lys Asn Arg His Asn Ala Glu Gly Arg Leu Ser Gly
                        610                 615                 620

Arg Ile Asn Asn Arg Phe Gly Asp Leu Asn Gly Ser Phe Ser Met Asn
        625                 630                 635                 640

Lys Asn Arg Asn Thr Asn Ser Thr Asn His Ser Leu Thr Gly Gly Tyr
                        645                 650                 655
```

```
Asn Ser Ser Phe Ala Leu Thr Ser Asp Gly Phe Tyr Trp Gly Gly Ser
            660                 665                 670

Thr Ala Gly Leu Thr Lys Leu Ala Gly Gly Ile Ile Lys Val Lys Ser
            675                 680                 685

Asn Asp Thr Lys Lys Asn Leu Val Lys Val Thr Gly Thr Leu Tyr Gly
        690                 695                 700

Asp Tyr Ser Leu Gly Ser Asn Asp Asn Ala Phe Ile Pro Val Pro Ala
705                 710                 715                 720

Leu Thr Pro Ala Ser Leu Ile Ile Glu Asp Asn Asn Tyr Gly Asp Asn
                725                 730                 735

Asn Ile Ser Ile Leu Ala Pro Thr Asn Asn Asp Met Phe Met Leu Pro
            740                 745                 750

Gly Asn Val Tyr Pro Val Glu Ile Glu Thr Lys Val Ser Val Ser Tyr
            755                 760                 765

Ile Gly Arg Gly Phe Asp Pro Asn Gly Thr Pro Leu Ser Gly Ala His
            770                 775                 780

Val Leu Asn Glu Pro His Val Ile Leu Asp Glu Asp Gly Gly Phe Ser
785                 790                 795                 800

Phe Glu Tyr Thr Gly Asn Glu Lys Thr Leu Phe Leu Leu Lys Gly Arg
                805                 810                 815

Thr Ile Tyr Thr Cys Gln Leu Gly Lys Asn Lys Val His Lys Gly Ile
            820                 825                 830

Val Phe Val Gly Asp Val Ile Cys Asp Ile Asn Ser Thr Ser Ser Leu
            835                 840                 845

Pro Asp Glu Phe Val Lys Asn Pro Arg Val Gln Asp Leu Leu Ala Lys
            850                 855                 860

Asn Asp Lys Gly
865

<210> SEQ ID NO 12
<211> LENGTH: 372
<212> TYPE: PRT
<213> ORGANISM: Artificial Sequence
<220> FEATURE:
<223> OTHER INFORMATION: Engineered E. coli CfaE peptide with
      Lactococcus signal peptide

<400> SEQUENCE: 12

Met Gln Arg Lys Lys Lys Gly Leu Ser Phe Leu Leu Ala Gly Thr Val
1               5                   10                  15

Ala Leu Gly Ala Leu Ala Val Leu Pro Val Gly Glu Ile Gln Ala Lys
            20                  25                  30

Ala Ala Ala Asp Lys Asn Pro Gly Ser Glu Asn Met Thr Asn Thr Ile
        35                  40                  45

Gly Pro His Asp Arg Gly Gly Ser Pro Ile Tyr Asn Ile Leu Asn
    50                  55                  60

Ser Tyr Leu Thr Ala Tyr Asn Gly Ser His His Leu Tyr Asp Arg Met
65                  70                  75                  80

Ser Phe Leu Cys Leu Ser Ser Gln Asn Thr Leu Asn Gly Ala Cys Pro
                85                  90                  95

Ser Ser Asp Ala Pro Gly Thr Ala Thr Ile Asp Gly Glu Thr Asn Ile
            100                 105                 110

Thr Leu Gln Phe Thr Glu Lys Arg Ser Leu Ile Lys Arg Glu Leu Gln
        115                 120                 125

Ile Lys Gly Tyr Lys Gln Phe Leu Phe Lys Asn Ala Asn Cys Pro Ser
```

```
                130                 135                 140
Lys Leu Ala Leu Asn Ser Ser His Phe Gln Cys Asn Arg Glu Gln Ala
145                 150                 155                 160

Ser Gly Ala Thr Leu Ser Leu Tyr Ile Pro Ala Gly Glu Leu Asn Lys
                165                 170                 175

Leu Pro Phe Gly Gly Val Trp Asn Ala Val Leu Lys Leu Asn Val Lys
                180                 185                 190

Arg Arg Tyr Asp Thr Thr Tyr Gly Thr Tyr Thr Ile Asn Ile Thr Val
                195                 200                 205

Asn Leu Thr Asp Lys Gly Asn Ile Gln Ile Trp Leu Pro Gln Phe Lys
                210                 215                 220

Ser Asn Ala Arg Val Asp Leu Asn Leu Arg Pro Thr Gly Gly Gly Thr
225                 230                 235                 240

Tyr Ile Gly Arg Asn Ser Val Asp Met Cys Phe Tyr Asp Gly Tyr Ser
                245                 250                 255

Thr Asn Ser Ser Ser Leu Glu Ile Arg Phe Gln Asp Asp Asn Ser Lys
                260                 265                 270

Ser Asp Gly Lys Phe Tyr Leu Lys Lys Ile Asn Asp Asp Ser Lys Glu
                275                 280                 285

Leu Val Tyr Thr Leu Ser Leu Leu Leu Ala Gly Lys Asn Leu Thr Pro
                290                 295                 300

Thr Asn Gly Gln Ala Leu Asn Ile Asn Thr Ala Ser Leu Glu Thr Asn
305                 310                 315                 320

Trp Asn Arg Ile Thr Ala Val Thr Met Pro Glu Ile Ser Val Pro Val
                325                 330                 335

Leu Cys Trp Pro Gly Arg Leu Gln Leu Asp Ala Lys Val Lys Asn Pro
                340                 345                 350

Glu Ala Gly Gln Tyr Met Gly Asn Ile Lys Ile Thr Phe Thr Pro Ser
                355                 360                 365

Ser Gln Thr Leu
    370
```

RECOMBINANT *LACTOCOCCUS LACTIS* EXPRESSING *ESCHERICHIA COLI* COLONIZATION FACTOR ANTIGEN I (CFA/I) FIMBRIAE AND THEIR METHODS OF USE

CROSS REFERENCE TO RELATED APPLICATIONS

This application claims priority to U.S. Provisional Application No. 61/704,672, filed Sep. 24, 2012, the entire contents of which are hereby incorporated by reference in their entirety for all purposes.

ACKNOWLEDGEMENT OF GOVERNMENTAL SUPPORT

This invention was made with government support under Contract No. NIH P01 AT004986, awarded by the National Institutes of Health. The government has certain rights in the invention.

FIELD

The present disclosure relates generally to therapeutic compositions comprising recombinant bacteria. Further, the disclosure elaborates upon methods of utilizing the taught therapeutic compositions to treat autoimmune and inflammatory disease. The present teachings also relate to the disclosed recombinant bacteria and methods of producing the recombinant bacteria utilized in the compositions and methods. Further taught herein are dietary supplements and food additive compositions comprising the taught recombinant bacteria.

BACKGROUND

Targeted immunotherapy is a highly developed approach for treating chronic infections, autoimmune diseases, allograft rejections, and malignancies. Immunotherapy for autoimmune disorders is also especially attractive for correcting inflammatory diseases without having to resort to immunosuppressive drug therapies. (Kochetkova, 2008).

Autoimmune diseases are characterized by the body's immune responses being directed against its own tissues, causing prolonged inflammation and subsequent tissue destruction. For instance, autoimmune disorders can cause immune-responsive cells to attack the linings of the joints or trigger immune cells to attack the insulin-producing islet cells of the pancreas, leading to rheumatoid arthritis and insulin-dependent diabetes mellitus respectively.

In contrast, a healthy immune system recognizes, identifies, remembers, attacks, and destroys bacteria, viruses, fungi, parasites, cancer cells, or any health-damaging agents not normally present in the body. A defective immune system, on the other hand, wreaks havoc throughout the host by directing antibodies against its own tissues as well as cell-mediated immune responses.

Generally, a disease in which cytotoxic cells are directed against self-antigens in the body's tissues is considered autoimmune in nature. Such diseases include celiac disease, Crohn's disease, pancreatitis, systemic lupus erythematosus, Sjogren's syndrome, Hashimoto's thyroiditis, and other endocrinopathies. Allergies and multiple sclerosis are also the result of disordered immune functioning.

Rheumatoid arthritis (RA) is an important autoimmune disease that inflicts roughly 0.5 to 1% of the human population worldwide. (Scott, 2010). In 2010, RA resulted in approximately 49,000 deaths globally. (Lozano, 2012). Rheumatoid arthritis results in a chronic, systemic inflammatory disorder that may affect many tissues and organs, but principally attacks synovial joints. RA can be a disabling and painful condition, which can lead to substantial loss of mobility if not adequately treated. The etiology of RA is still unknown, but hereditary factors and possible infectious agents (bacteria and viruses) are assumed to participate in the disease initiation. (Kochetkova, 2008). RA is mediated by T cells, predominantly $CD4^+$ T cells, and proinflammatory cytokines, such as TNF-α and IL-1, are considered responsible for orchestrating pathogenesis. Id.

The design of therapeutic agents and vaccines capable of preventing or reversing chronic inflammation is of particular interest to the medical community.

Thus, the development of such a therapeutic is urgently needed in the art.

Furthermore, there is a need in the art for dietary supplements and food additives comprising elements that are beneficial to a subject's immune response.

BRIEF SUMMARY

The present disclosure addresses a critical need in the medical community by developing a recombinant Gram-positive bacterial vector that successfully expresses enterotoxigenic *Escherichia coli* colonization factor antigen I fimbriae.

Before the present disclosure, there had not been a successful expression of enterotoxigenic *E. coli* (ETEC) colonization factor antigen I (CFA/I) fimbriae in Gram-positive bacteria. The present inventors have surprisingly discovered that through the methods taught herein, one is able to insert and successfully express, *E. coli* CFA/I fimbriae in a Gram-positive bacteria.

The disclosure therefore presents therapeutic compositions comprising recombinant Gram-positive bacteria expressing ETEC CFA/I fimbriae that are beneficial for treating an autoimmune disease or disorder.

Furthermore, the present therapeutic compositions comprising the recombinant Gram-positive bacteria expressing ETEC CFA/I fimbriae are beneficial for treating an inflammatory disease or disorder.

The product produced by the recombinant bacteria taught herein provides beneficial properties for the treatment of autoimmune and inflammatory diseases. That is, the peptide sequences expressed by the taught recombinant bacteria are demonstrated to be beneficial for the treatment of autoimmune and inflammatory diseases.

In a particular embodiment, the recombinant Gram-positive bacteria expressing the ETEC CFA/I fimbriae belong to the lactic acid bacterial clade. Some embodiments utilize members of the Order Lactobacillales as the recombinant bacterial host for the ETEC CFA/I fimbriae gene. Yet other embodiments employ members of the Family Streptococcaceae as the recombinant bacterial host for the ETEC CFA/I fimbriae gene. Yet still other embodiments use bacteria from the Genus *Lactococcus* to host the ETEC CFA/I fimbriae gene. One particular embodiment, utilizes the bacterial Species *Lactococcus lactis* to host the ETEC CFA/I fimbriae gene.

The compositions presented herein are suitable for combination with any known pharmaceutically acceptable carrier, buffer, excipient, adjuvant, or mixture thereof.

The compositions presented herein may in some embodiments be placed within foodstuffs, such as: beverages, dairy products, yogurts, fermented food products, and the like, as feasible and consumer friendly delivery vehicles.

The compositions taught herein may also be delivered in food supplements, such as: powdered compositions comprising the taught recombinant bacterial cells, encapsulated compositions comprising the taught recombinant bacterial cells, or any liquid formulation comprising the taught recombinant bacterial cells.

In embodiments, the recombinant Gram-positive bacterial cell comprising a nucleotide sequence coding for ETEC CFA/I fimbriae comprises sequences coding for at least one gene selected from the group consisting of cfaA, cfaB, cfaC, and cfaE.

In certain embodiments, the recombinant Gram-positive bacterial cells contain nucleotide sequences coding for the cfaA gene. In other embodiments, the recombinant Gram-positive bacterial cells contain nucleotide sequences coding for the cfaB gene. In yet other embodiments, the recombinant Gram-positive bacterial cells contain nucleotide sequences coding for the cfaC gene. Further still, the recombinant Gram-positive bacterial cells may contain nucleotide sequences coding for the cfaE gene. Also disclosed are recombinant Gram-positive bacterial cells containing nucleotide sequences coding for the cfaB and cfaE gene.

In certain embodiments, the recombinant Gram-positive bacteria comprising a nucleotide sequence coding for at least one gene selected from the group consisting of cfaA, cfaB, cfaC, and cfaE, is a bacteria from the Genus *Lactococcus*.

In certain embodiments, a recombinant *Lactococcus* bacterial cell contains nucleotide sequences coding for the cfaA gene. In other embodiments, a recombinant *Lactococcus* bacterial cell contains nucleotide sequences coding for the cfaB gene. In yet other embodiments, a recombinant *Lactococcus* bacterial cell contains nucleotide sequences coding for the cfaC gene. Further still, a recombinant *Lactococcus* bacterial cell may contain nucleotide sequences coding for the cfaE gene. Also disclosed are recombinant *Lactococcus* bacterial cells containing nucleotide sequences coding for the cfaB and cfaE gene.

In certain embodiments, the recombinant Gram-positive bacteria comprising a nucleotide sequence coding for at least one gene selected from the group consisting of cfaA, cfaB, cfaC, and cfaE, is a *Lactococcus lactis* bacterial species.

In certain embodiments, a recombinant *Lactococcus lactis* bacterial cell contains nucleotide sequences coding for the cfaA gene. In other embodiments, a recombinant *Lactococcus lactis* bacterial cell contains nucleotide sequences coding for the cfaB gene. In yet other embodiments, a recombinant *Lactococcus lactis* bacterial cell contains nucleotide sequences coding for the cfaC gene. Further still, a recombinant *Lactococcus lactis* bacterial cell may contain nucleotide sequences coding for the cfaE gene. Also disclosed are recombinant *Lactococcus lactis* bacterial cells containing nucleotide sequences coding for the cfaB and cfaE gene.

In embodiments, the recombinant Gram-positive bacterial cell comprising a nucleotide sequence coding for ETEC CFA/I fimbriae comprises sequences coding for at least one gene selected from the group consisting of cfaA, cfaB, cfaC, and cfaE, and at least one of these genes are expressed by the Gram-positive bacterial cell.

In some embodiments, the cfaA gene is expressed in the Gram-positive bacteria. In other embodiments, the cfaB gene is expressed in the Gram-positive bacteria. In yet other embodiments, the cfaC gene is expressed in the Gram-positive bacteria. Yet other embodiments demonstrate that the cfaE gene is expressed in the Gram-positive bacteria. Furthermore, any combination of the aforementioned genes can be expressed in the Gram-positive bacteria, for instance in some embodiments both the cfaB and cfaE genes are expressed.

In embodiments, the recombinant *Lactococcus* bacterial cell comprising a nucleotide sequence coding for ETEC CFA/I fimbriae comprises sequences coding for at least one gene selected from the group consisting of cfaA, cfaB, cfaC, and cfaE, and at least one of these genes are expressed by the *Lactococcus* bacterial cell.

In some embodiments, the cfaA gene is expressed in the *Lactococcus* bacterial cell. In other embodiments, the cfaB gene is expressed in the *Lactococcus* bacterial cell. In yet other embodiments, the cfaC gene is expressed in the *Lactococcus* bacterial cell. Yet other embodiments demonstrate that the cfaE gene is expressed in the *Lactococcus* bacterial cell. Furthermore, any combination of the aforementioned genes can be expressed in the *Lactococcus* bacterial cell, for instance in some embodiments both the cfaB and cfaE genes are expressed.

In embodiments, the recombinant *Lactococcus lactis* bacterial cell comprising a nucleotide sequence coding for ETEC CFA/I fimbriae comprises sequences coding for at least one gene selected from the group consisting of cfaA, cfaB, cfaC, and cfaE, and at least one of these genes are expressed by the *Lactococcus lactis* bacterial cell.

In some embodiments, the cfaA gene is expressed in the *Lactococcus lactis* bacterial cell. In other embodiments, the cfaB gene is expressed in the *Lactococcus lactis* bacterial cell. In yet other embodiments, the cfaC gene is expressed in the *Lactococcus lactis* bacterial cell. Yet other embodiments demonstrate that the cfaE gene is expressed in the *Lactococcus lactis* bacterial cell. Furthermore, any combination of the aforementioned genes can be expressed in the *Lactococcus lactis* bacterial cell, for instance in some embodiments both the cfaB and cfaE genes are expressed.

In embodiments, the recombinant Gram-positive bacterial cell comprising a nucleotide sequence coding for ETEC CFA/I fimbriae comprises SEQ ID NO: 1. In some embodiments, the recombinant Gram-positive bacterial cell expresses SEQ ID NO: 1.

In embodiments, the recombinant *Lactococcus* bacterial cell comprising a nucleotide sequence coding for ETEC CFA/I fimbriae comprises SEQ ID NO: 1. In some embodiments, the recombinant *Lactococcus* bacterial cell expresses SEQ ID NO: 1.

In embodiments, the recombinant *Lactococcus lactis* bacterial cell comprising a nucleotide sequence coding for ETEC CFA/I fimbriae comprises SEQ ID NO: 1. In some embodiments, the recombinant *Lactococcus lactis* bacterial cell expresses SEQ ID NO: 1.

In yet other embodiments, the recombinant Gram-positive bacterial cell comprising a nucleotide sequence coding for ETEC CFA/I fimbriae comprises sequences coding for at least one gene selected from the group consisting of SEQ ID NOs: 2, 3, 4, and 5. In some embodiments, the recombinant Gram-positive bacterial cell expresses at least one gene selected from the group consisting of SEQ ID NOs: 2, 3, 4, and 5. In some embodiments, SEQ ID NO: 2 is expressed. In other embodiments, SEQ ID NO: 3 is expressed. Further, embodiments entail cells that express SEQ ID NO: 4. Yet other embodiments entail cells that express SEQ ID NO: 5. Also taught are embodiments in which SEQ ID NO: 2 and SEQ ID NO: 5 are both expressed. The disclosure also teaches cells in which any combination of the aforementioned SEQ ID NOs is expressed.

Further, the disclosure teaches Gram-positive recombinant bacteria that express at least one peptide selected from the group consisting of SEQ ID NO: 9, 10, 11, and 12, or combinations thereof.

In yet other embodiments, the recombinant *Lactococcus* bacterial cell comprising a nucleotide sequence coding for ETEC CFA/I fimbriae comprises sequences coding for at least one gene selected from the group consisting of SEQ ID NOs: 2, 3, 4, and 5. In some embodiments, the recombinant *Lactococcus* bacterial cell expresses at least one gene selected from the group consisting of SEQ ID NOs: 2, 3, 4, and 5. In some embodiments, SEQ ID NO: 2 is expressed. In other embodiments, SEQ ID NO: 3 is expressed. Further, embodiments entail cells that express SEQ ID NO: 4. Yet other embodiments entail cells that express SEQ ID NO: 5. Also taught are embodiments in which SEQ ID NO: 2 and SEQ ID NO: 5 are both expressed. The disclosure also teaches cells in which any combination of the aforementioned SEQ ID NOs is expressed.

Further, the disclosure teaches *Lactococcus* recombinant bacteria that express at least one peptide selected from the group consisting of SEQ ID NO: 9, 10, 11, and 12, or combinations thereof.

In yet other embodiments, the recombinant *Lactococcus lactis* bacterial cell comprising a nucleotide sequence coding for ETEC CFA/I fimbriae comprises sequences coding for at least one gene selected from the group consisting of SEQ ID NOs: 2, 3, 4, and 5. In some embodiments, the recombinant *Lactococcus lactis* bacterial cell expresses at least one gene selected from the group consisting of SEQ ID NOs: 2, 3, 4, and 5. In some embodiments, SEQ ID NO: 2 is expressed. In other embodiments, SEQ ID NO: 3 is expressed. Further, embodiments entail cells that express SEQ ID NO: 4. Yet other embodiments entail cells that express SEQ ID NO: 5. Also taught are embodiments in which SEQ ID NO: 2 and SEQ ID NO: 5 are both expressed. The disclosure also teaches cells in which any combination of the aforementioned SEQ ID NOs is expressed.

Further, the disclosure teaches *Lactococcus lactis* recombinant bacteria that express at least one peptide selected from the group consisting of SEQ ID NO: 9, 10, 11, and 12, or combinations thereof.

Also taught herein are recombinant Gram-positive bacterial cells, *Lactococcus* bacterial cells, and *Lactococcus lactis* bacterial cells, for example, comprising a nucleotide sequence coding for ETEC CFA/I fimbriae comprising SEQ ID NO: 1, or nucleotide sequences sharing 99% sequence homology to SEQ ID NO: 1, or 98% sequence homology to SEQ ID NO: 1, or 97% sequence homology to SEQ ID NO: 1, or 96% sequence homology to SEQ ID NO: 1, or 95% sequence homology to SEQ ID NO: 1, or 95% to 90% sequence homology to SEQ ID NO: 1.

Furthermore, also taught herein are recombinant Gram-positive bacterial cells, *Lactococcus* bacterial cells, and *Lactococcus lactis* bacterial cells, for example, comprising a nucleotide sequence coding for ETEC CFA/I fimbriae comprising SEQ ID NO: 1, or nucleotide sequences with single point mutations, or single nucleotide substitutions, within SEQ ID NO: 1, wherein said single point mutations, or single nucleotide substitutions, are silent and do not effect the protein coded for by SEQ ID NO: 1.

Also taught herein are recombinant Gram-positive bacterial cells, *Lactococcus* bacterial cells, and *Lactococcus lactis* bacterial cells, for example, comprising a nucleotide sequence coding for ETEC CFA/I fimbriae comprising at least one gene selected from the group consisting of SEQ ID NOs: 2, 3, 4, and 5, or nucleotide sequences sharing 99% sequence homology to SEQ ID NOs: 2, 3, 4, and 5, or 98% sequence homology to SEQ ID NOs: 2, 3, 4, and 5, or 97% sequence homology to SEQ ID NOs: 2, 3, 4, and 5, or 96% sequence homology to SEQ ID NOs: 2, 3, 4, and 5, or 95% sequence homology to SEQ ID NOs: 2, 3, 4, and 5, or 95% to 90% sequence homology to SEQ ID NOs: 2, 3, 4, and 5.

Furthermore, also taught herein are recombinant Gram-positive bacterial cells, *Lactococcus* bacterial cells, and *Lactococcus lactis* bacterial cells, for example, comprising a nucleotide sequence coding for ETEC CFA/I fimbriae comprising at least one gene selected from the group consisting of SEQ ID NOs: 2, 3, 4, and 5, or nucleotide sequences with single point mutations, or single nucleotide substitutions, within SEQ ID NOs: 2, 3, 4, and 5, wherein said single point mutations, or single nucleotide substitutions, are silent and do not effect the proteins coded for by SEQ ID NOs: 2, 3, 4, and 5.

Also taught herein are recombinant Gram-positive bacterial cells, *Lactococcus* bacterial cells, and *Lactococcus lactis* bacterial cells, for example, comprising a nucleotide sequence coding for ETEC CFA/I fimbriae comprising sequences coding for at least one gene selected from the group consisting of cfaA, cfaB, cfaC, and cfaE, or nucleotide sequence corresponding to the aforementioned structural genes that have been codon optimized for expression. That is, codon optimization procedures may be performed on each of the genes individually in order to maximize expression into a particular Gram-positive bacterial species.

Furthermore, also taught herein are recombinant Gram-positive bacterial cells, *Lactococcus* bacterial cells, and *Lactococcus lactis* bacterial cells, for example, expressing at least one peptide selected from the group consisting of SEQ ID NO: 9, 10, 11, and 12, or combinations thereof. In some embodiments, the peptides of SEQ ID NO: 9 and SEQ ID NO: 12 are expressed.

Furthermore, in embodiments, the entire CFA/I operon may be codon optimized for maximum expression into a particular recipient Gram-positive bacterial species.

The recombinant bacterial cells taught herein comprising a nucleotide sequence coding for ETEC CFA/I fimbriae can induce an anti-inflammatory response in a subject administered the recombinant bacterial cell.

In some embodiments, the level of a regulatory cytokine selected from IL-10 or TGF-β in a subject is increased upon administering of the recombinant bacteria to the subject, as compared to the level of the regulatory cytokine IL-10 or TGF-β present in the subject before said administering of the recombinant bacteria.

In other aspects, the level of at least one cytokine selected from the group consisting of IFN-γ, TNF-α, and IL-17 in a subject is decreased upon administering of the recombinant bacteria to the subject, as compared to the level of at least one of the cytokines selected from the group consisting of IFN-γ, TNF-α, and IL-17 present in the subject before said administering of the recombinant bacteria.

Further taught herein are probiotic compositions comprising recombinant lactic acid bacteria expressing ETEC CFA/I fimbriae. In certain aspects, the taught probiotic compositions support a healthy immune system. The taught probiotic compositions may also be used to supplement an individual's normal dietary regime.

Furthermore, in certain embodiments, the present disclosure teaches dietary supplements that comprise recombinant bacteria comprising nucleotide sequences encoding ETEC CFA/I fimbriae. In particular embodiments, the recombinant bacteria expresses the ETEC CFA/I fimbriae. In certain aspects, the taught dietary supplements support a healthy immune system. The dietary supplements may also be used to supplement an individual's normal dietary regime.

The present disclosure also teaches food additive compositions comprising recombinant Gram-positive bacteria comprising nucleotide sequences encoding ETEC CFA/I fimbriae. In particular embodiments, the recombinant Gram-positive bacteria expresses the ETEC CFA/I fimbriae.

In some embodiments, the taught food additive compositions comprise recombinant lactic acid bacteria comprising nucleotide sequences encoding ETEC CFA/I fimbriae. In particular embodiments, the recombinant lactic acid bacteria expresses the ETEC CFA/I fimbriae.

In other embodiments, the taught food additive compositions comprise recombinant *Lactococcus* bacteria comprising nucleotide sequences encoding ETEC CFA/I fimbriae. In particular embodiments, the recombinant *Lactococcus* bacteria expresses the ETEC CFA/I fimbriae.

In yet other embodiments, the taught food additives comprise recombinant *Lactococcus lactis* bacteria comprising nucleotide sequences encoding ETEC CFA/I fimbriae. In particular embodiments, the recombinant *Lactococcus lactis* bacteria expresses the ETEC CFA/I fimbriae.

In certain aspects, the taught food additives support a healthy immune system.

Also presented herein are methods of treating or preventing an autoimmune or inflammatory disease by administering the aforementioned compositions comprising a recombinant bacteria comprising a nucleotide sequence coding for enterotoxigenic *Escherichia coli* colonization factor antigen I fimbriae.

In an embodiment, the method of treating or preventing an autoimmune or inflammatory disease comprises administering the taught compositions comprising the recombinant bacteria once daily to a subject in need of such treatment.

In another embodiment, the method of treating or preventing an autoimmune or inflammatory disease comprises administering the taught compositions comprising the recombinant bacteria twice daily, three times daily, four times daily, or five times daily to a subject in need of such treatment.

Other embodiments comprise administering the taught compositions comprising the recombinant bacteria on an as needed basis based upon a subject's physiological symptoms, such as pain, swelling, irritation, or discomfort.

Some embodiments comprise administering the taught compositions comprising the recombinant bacteria on a prophylactic bases to a subject that does not presently experience physiological symptoms associated with an autoimmune or inflammatory disease.

Taught embodiments comprise administering the disclosed compositions comprising the recombinant bacteria, wherein the compositions are combined with any known pharmaceutically acceptable carrier, buffer, excipient, adjuvant, or mixture thereof.

Taught embodiments entail administering the disclosed compositions comprising the recombinant bacteria, as part of a subject's dietary routine via a foodstuff, such as a: beverage, dairy product, yogurt, fermented food, or the like.

Taught embodiments entail administering the disclosed compositions comprising the recombinant bacteria, as part of a food supplement, such as a: powdered composition, encapsulated composition, or any liquid formulation.

The methods disclosed herein are able to increase the level of a regulatory cytokine selected from IL-10 or TGF-β in a subject, upon administering the disclosed compositions, as compared to the level of the regulatory cytokine IL-10 or TGF-β present in the subject before said administering.

The methods disclosed herein are able to decrease the level of at least one cytokine selected from the group consisting of IFN-γ, TNF-α, and IL-17 in a subject, upon administering the disclosed compositions, as compared to the level of at least one of the cytokines selected from the group consisting of IFN-γ, TNF-α, and IL-17 present in the subject before said administering.

Also presented herein are methods of treating or preventing rheumatoid arthritis. Other methods taught herein are for treating or preventing multiple sclerosis.

In some embodiments, rheumatoid arthritis is treated by administering the taught compositions in conjunction with palliative arthritic treatments, as the disclosed compositions are demonstrated to suppress the level of proinflammatory cytokines and increase the level of anti-inflammatory cytokines. Thus, the present methods may act synergistically with known arthritic treatments to relieve swelling and joint pain.

Also presented herein are methods of eliciting an immune response in an individual, comprising: administering the aforementioned compositions comprising a recombinant Gram-positive bacteria comprising a nucleotide sequence coding for enterotoxigenic *Escherichia coli* colonization factor antigen I fimbriae.

The present disclosure also relates to methods of suppressing proinflammatory cytokines in an individual by administering a composition comprising recombinant Gram-positive bacteria comprising a nucleotide sequence coding for enterotoxigenic *Escherichia coli* colonization factor antigen I fimbriae. In some embodiments, the proinflammatory cytokine suppressed by the present methods are at least one selected from the group consisting of IFN-γ, TNF-α, and IL-17.

In particular embodiments, the present methods decrease the level of proinflammatory cytokines produced in a subject treated with the taught compositions to an extent greater than the level of proinflammatory cytokines that would be depressed by the same subject if treated with a *Salmonella* vector expressing CFA/I fimbriae. In some embodiments, the proinflammatory cytokine suppressed by the present methods are at least one selected from the group consisting of IFN-γ, TNF-α, and IL-17.

Furthermore, the present disclosure teaches methods of increasing anti-inflammatory cytokines in an individual by administering a composition comprising recombinant Gram-positive bacteria comprising a nucleotide sequence coding for enterotoxigenic *Escherichia coli* colonization factor antigen I fimbriae. In some embodiments, the anti-inflammatory cytokine increased by the present methods is IL-10 or TGF-β.

In particular embodiments, the present methods increase the level of anti-inflammatory cytokines produced in a subject treated with the taught compositions to an extent greater than the level of anti-inflammatory cytokines that would be produced by the same subject if treated with a *Salmonella* vector expressing CFA/I fimbriae. In some embodiments, the anti-inflammatory cytokines are IL-10 or TGF-β.

In some embodiments, a subject treated with the taught compositions according to the present methods will produce minimal anti-CFA/I fimbriae antibodies.

In particular embodiments, the amount of anti-CFA/I fimbriae antibodies produced in a subject treated with the taught compositions is at least 50%, at least 60%, at least 70%, at least 80%, at least 90%, at least 95%, at least 99%, or at least 100% lower than the amount of anti-CFA/I fimbriae antibodies that would be produced in the same subject if that subject was administered a *Salmonella* vector expressing CFA/I fimbriae.

Also taught herein are methods for producing a composition for the treatment of an autoimmune or inflammatory disease, comprising: introducing a nucleotide sequence coding for enterotoxigenic *Escherichia coli* colonization factor antigen I fimbriae into a recipient Gram-positive bacterial cell, e.g. a lactic acid bacterial cell, and culturing the recipient bacterial cell under conditions which allow for expression of the enterotoxigenic *Escherichia coli* colonization factor antigen I fimbriae.

The methods may further comprise packaging the recombinant bacterial cells with any pharmaceutically acceptable carrier, buffer, excipient, adjuvant, or mixture thereof.

The methods may further comprise packaging the recombinant bacterial cells with any foodstuff, such as a: beverage, dairy product, yogurt, fermented food, or the like.

The methods may further comprise packaging the recombinant bacterial cells with a food supplement, such as a: powdered composition, encapsulated composition, or any liquid formulation.

The recombinant bacterial cells taught herein may be live upon administration or may not. Further, the therapeutic compositions disclosed herein may comprise mixtures of both live and non-living recombinant bacterial cells.

SEQUENCES OF THE INVENTION

Figure 1:
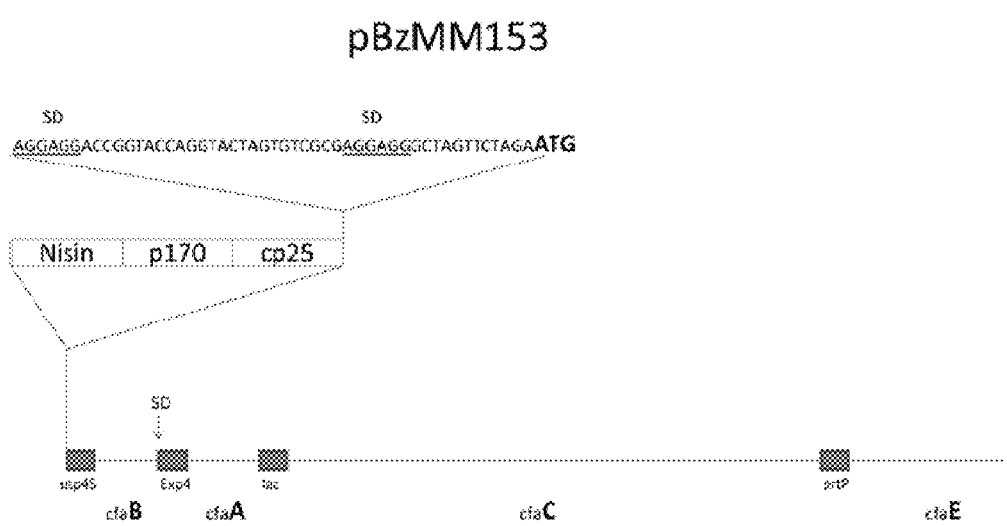
FIG. 1 illustrates an engineered pBzMM153 operon that was modified from the native enterotoxigenic *Escherichia coli* colonization factor antigen I operon, i.e. cfaI operon. The figure demonstrates that the native gene sequence of cfaA, cfaB, cfaC, cfaE has been engineered to instead comprise cfaB, cfaA, cfaC, cfaE. Furthermore, the figure illustrates the placement of the: Nisin, P170, and CP25 promoters, as well as the in-frame replacement of the native signal sequences with usp45, Exp4, lac, and prtP signal sequences, along with the three Shine-Dalgarno sequences. The Shine-Dalgarno sequences are denoted "SD." The engineered operon is contained in SEQ ID NO: 1.
Figure 2:
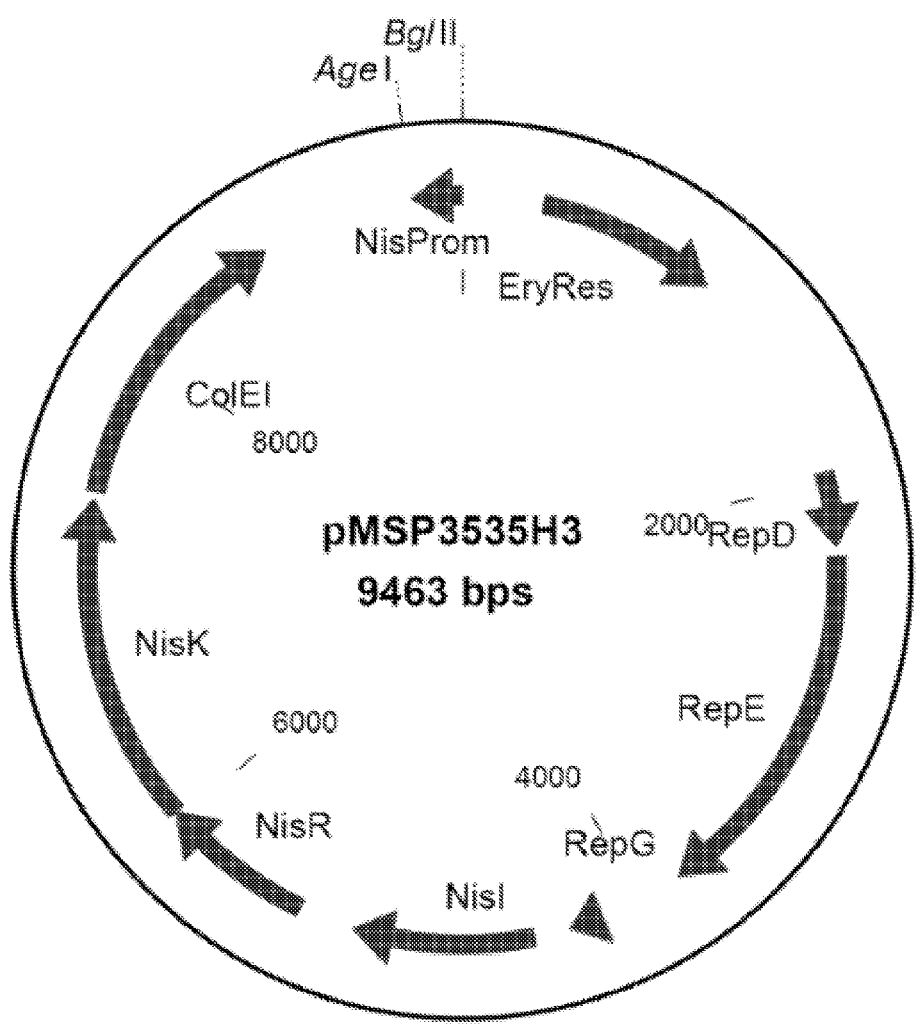
FIG. 2 illustrates an engineered recombinant plasmid construct according to the present disclosure.

Sequence listings for SEQ ID Nos: 1-12 are part of this application and are incorporated by reference herein. A paper copy of the Sequence listings is provided at the end of this document and a CRF copy is submitted concurrently herewith.

DETAILED DESCRIPTION

Detailed descriptions of one or more preferred embodiments are provided herein. It is to be understood, however, that the present disclosure may be embodied in various forms. Therefore, specific details disclosed herein are not to be interpreted as limiting, but rather as a basis for the claims and as a representative basis for teaching one skilled in the art to employ the present disclosure in any appropriate manner.

The following description includes information that may be useful in understanding the present disclosure. It is not an admission that any of the information provided herein is prior art, or that any publication specifically or implicitly referenced is prior art.

Unless defined otherwise, all technical and scientific terms used herein have the same meaning as commonly understood by one of ordinary skill in the art to which this disclosure belongs.

DEFINITIONS

As used herein, the use of the word "a" "an" or "the" can mean one or more than one.

Numbers and numerical ranges recited herein are to be understood to be modified by the term "about" as would be understood by one of ordinary skill in the art.

As used herein, the term "adjuvant" refers to a substance sometimes included in a vaccine or therapeutic formulation to enhance or modify the immune-stimulating properties of the vaccine or therapeutic formulation.

As used herein, the term "antigen" refers to a substance that triggers an immune system response, resulting in production of an antibody specific for the antigen. Thus, an antigen is a substance that binds specifically to a respective antibody.

As used herein, the term "operon" refers to a cluster or series of adjacent structural genes that are transcribed as a unit into a single mRNA molecule. The cluster or series of adjacent structural genes can be under the control of a single promoter and also under the control of a composite tandem promoter.

As used herein, the term "autoimmune disease" refers to a physiological condition in a subject that is resultant from the subject's own body producing an inappropriate immune response that targets and damages the subject's own cells.

As used herein, the term "inflammatory disease" encompasses any disease or condition characterized by inflammation. Inflammation is a basic physiological response to a variety of external or internal insults, such as infectious agents, physical injury, hypoxia, or disease processes. Therefore, diseases or conditions falling within "inflammatory disease" do not have to share a common genetic or physiological basis, so long as the disease or condition results in inflammation.

As used herein, the term "recombinant bacteria" refers to bacteria that have been genetically modified from their native state. For instance, recombinant bacteria may have nucleotide insertions, nucleotide deletions, nucleotide rearrangements, and nucleotide modifications introduced into the bacterial DNA. Further, recombinant bacteria may comprise exogenous nucleotide sequences on plasmids or exogenous nucleotide sequences stably incorporated into the chromosomal DNA.

As used herein, and in light of the previous definition, the term "recombinant lactic acid bacterial cell" refers to lactic acid bacterial cells that have been genetically modified from their native state. In some aspects of the disclosure, for example, a "recombinant lactic acid bacterial cell" comprises exogenous nucleotide sequences from Gram-negative bacteria.

As used herein, the term "probiotic microorganism" is a microorganism which has a beneficial effect on a host's intestinal microflora ecology, presumably by promoting the growth of so-called "good" microorganisms, inhibiting the growth of so-called "bad" microorganisms, or by performing metabolic activities that are beneficial to the host. In particular embodiments herein, the disclosed recombinant bacteria perform metabolic functions that are beneficial to a host. In certain embodiments, the recombinant bacteria are lactic acid bacteria, a common probiotic bacterial clade.

Arming the Mucosa with Recombinant *Lactococcus lactis* Expressing ETEC CFA/I Fimbriae A potential method that has been proposed to treat autoimmune and inflammatory diseases, such as RA, is the delivery of enterotoxigenic *Escherichia coli* (ETEC) colonization factor antigen I (CFA/I) fimbriae via live attenuated *Salmonella* vectors. (See, e.g., Kochetkova, 2008).

However, despite the possibility of utilizing attenuated *Salmonella* to deliver CFA/I fimbriae to induce anti-inflammatory immune responses in an individual, there remain significant drawbacks to this technology.

For instance, *Salmonella* is a Gram-negative bacterial species, which means that the bacterium's cell wall will invariably be associated with the endotoxic lipopolysaccharide complex (LPS) associated with the outer membrane of Gram-negative bacteria.

LPS, also known as lipoglycans, are large molecules consisting of a lipid and polysaccharide joined by a covalent bond and are found in the outer membrane of Gram-negative bacteria. LPS act as endotoxins and elicit strong immune responses in animals. In humans, LPS triggers an innate immune response characterized by cytokine production and immune system activation. Inflammation is a common result of cytokine production, which can also produce host toxicity.

Consequently, any therapeutic effects associated with the utilization of a Gram-negative bacterium, such as *Salmonella*, as a delivery vector for anti-inflammatory disease treatment will likely be counterbalanced by the ensuing immune response and associated inflammation resulting from the presence of LPS in these bacterial vectors.

A second concern with the utilization of *Salmonella* based delivery vectors concerns the inherent potential of these delivery systems to revert back to a virulent state. A possible solution to this concern involves introducing multiple virulence attenuating mutations into the bacterial vector. However, these mutations should be capable of attenuation independently. This possible solution adds increased complexity and cost to developing effective attenuated *Salmonella* delivery vectors.

Another risk with using pathogenic bacteria as vaccine vectors is complications that can arise due to pre-existing immunity. Prior exposure to the bacterial vector has been demonstrated to decrease efficacy of the vaccine. (Attridge, 1997). Attridge reported that the effectiveness of utilizing attenuated *Salmonella* to deliver *E. coli* fimbrial proteins to the gut-associated lymphoid tissue of mice "were dramatically impaired" in recipients "with pre-existing immunity to the vector strain." Id. at Abstract.

Furthermore, there is a risk with attenuated *Salmonella* based vector systems that the bacterium may easily transfer genetic material to other Gram-negative bacteria resident in the treated host. Scholars have warned that bacterial based vector systems "[e]specially bacteria carrying recombinant plasmids" face an increased risk of "the probability of horizontal gene transfer to other bacteria present" in the host. (Detmer, 2006).

This horizontal gene transfer is especially problematic when considering the possibility of an attenuated *Salmonella* strain horizontally transferring genetic information to native *Salmonella* or other Gram-negative strains present in the recipient.

Thus, there is an urgent need in the art for the development of safer bacterial based therapeutics and vaccines that are not reliant upon attenuated invasive bacterial strains and therefore do not suffer from the aforementioned drawbacks.

With respect to bacterial based expression vectors, such as the *Salmonella* vectors expressing CFA/I fimbriae, there is a complete dearth of development in the area of expressing CFA/I fimbriae in Gram-positive bacterial delivery systems.

The development of a Gram-positive bacterial vector therapeutic for the expression of CFA/I fimbriae would not suffer from the drawbacks present in the art.

Specifically, the development of a Gram-positive delivery system for CFA/I fimbriae, in a bacterial species that has been accorded a Generally Recognized as Safe (GRAS) status, would offer consumers suffering from autoimmune and inflammatory disease a superior alternative to the present bacterial delivery systems expressing CFA/I fimbriae in attenuated *Salmonella*.

Most mammalian pathogens invade the host through a mucosal surface, thus arming the mucosa will ultimately prevent pathogens from initiating infection.

Mucosal immunity is accomplished by facilitating vaccine uptake to mucosal inductive tissues. At the inductive sites, foreign proteins or materials referred to as antigens, are sampled and used to trigger a host immune response. Mucosal inductive sites are present in the gut known as Peyer's patches, and in the upper respiratory tract referred to as nasal-associated lymphoid tissues (NALT) or in humans, referred to as Waldeyer's ring (tonsils and adenoids).

Once antigens are sampled and processed, they will induce memory lymphocyte responses in mucosal effector tissues, which are the various mucosal surfaces of the gut, respiratory tract, and genitourinary tract. These mucosal effector sites contain memory B and T lymphocytes, antigen presenting cells (APCs), as well as a plethora of other cell types with different functions in the mucosal network that ultimately determines the outcome of the immune response.

Without wishing to be bound to a particular theory, the present inventors hypothesize that some, but not all, of the molecules that pathogens use to dock to target cells may at the same time down-regulate the immune system.

In the present disclosure, the inventors have shown that the hypothesis is not only correct, but that when applied appropriately can lead to the development of novel therapeutic compositions that are useful for the treatment of autoimmune disorders and inflammatory disease.

As will be detailed below, the inventors have developed a recombinant *Lactococcus lactis* expressing ETEC CFA/I fimbriae, that when orally delivered to mice, is able to prevent the symptoms and to block the progression of collagen-induced arthritis (CIA).

CIA is a model of rheumatoid arthritis and therefore implicates the ability of the recombinant bacteria taught herein to be an effective treatment for this highly pervasive autoimmune disease.

Further, the inventors have developed a recombinant *Lactococcus lactis* expressing ETEC CFA/I fimbriae, that when orally delivered to mice, is able to prevent the symptoms and to block the progression of experimental autoimmune encephalomyelitis (EAE).

EAE is a model for multiple sclerosis and therefore implicates the ability of the recombinant bacteria taught herein to be an effective treatment for this autoimmune disease.

Thus, the present inventors have illustrated that the recombinant *Lactococcus lactis* expressing ETEC CFA/I fimbriae have strong potential to act as multi-purpose modulators of pathological immune response in absence of an autoantigen.

These discoveries have profound implications for the treatment and prevention of autoimmune diseases like rheumatoid arthritis and other inflammatory diseases.

Lactic Acid Bacteria

Presently, the only recognized bacterial delivery systems for ETEC CFA/I fimbriae are based upon Gram-negative bacteria. Specifically, the *Salmonella* based vector system and its drawbacks have been discussed.

The disclosure herein represents a departure from the expectations of the art, by surprisingly showing for the first time, that ETEC CFA/I fimbriae can be successfully expressed in a Gram-positive bacterial vector system. That is, the disclosure presents a lactic acid bacterium, *Lactococcus lactis*, which comprises an engineered plasmid containing a nucleotide sequence coding for ETEC CFA/I fimbriae. The nucleotide sequence is shown to be expressed in the *Lactococcus lactis* system.

Lactic Acid Bacteria Classification

The lactic acid bacteria comprise a clade of Gram-positive bacteria associated by their common metabolic and physiological characteristics. For instance, these bacteria have low-GC, are acid-tolerant, are generally non-sporulating and non-respiring, rod-shaped bacilli or cocci phenotypes. As their name implies, lactic acid bacteria produce lactic acid as the major metabolic end-product of carbohydrate fermentation.

The order Lactobacillales comprises the lactic acid bacteria. Families present in the Lactobacillales include: Aerococcaceae, Carnobacteriaceae, Enterococcaceae, Lactobacillaceae, Leuconostocaceae, and Streptococcaceae. A representative genus of Streptococcaceae is *Lactococcus*. A representative species of *Lactococcus* is *Lactococcus lactis*.

The aforementioned is not an exhaustive list of the members of the lactic acid bacteria, but is merely illustrative of the structuring of the group. One of skill in the art would be able to ascertain the members of the lactic acid bacteria.

The present disclosure utilizes *Lactococcus* bacteria in the exemplary embodiments, but it would be within the skill of one in the art to utilize the taught methods for expression of ETEC CFA/I fimbriae in other lactic acid bacteria. For example, the disclosed promoter sequences along with the taught signal sequence coding regions (encoding the signal sequence peptides) are engineered for lactic acid bacteria and would be useful for deployment in other lactic acid bacterial species.

For example, as taught herein, the native order of structural genes present in the cfaI operon has been altered from cfaA, cfaB, cfaC, and cfaE to the engineered order of cfaB, cfaA, cfaC, and cfaE. This structural rearrangement of operon genes is expected to be expressible in other lactic acid bacteria.

One of skill in the art would be able to utilize the disclosed methods to insert the engineered cfaB, cfaA, cfaC, and cfaE structural gene sequence, with appropriate signal sequence coding regions for the particular lactic acid bacterial recipient, into a recipient lactic acid bacterial cell and obtain expression of CFA/I fimbriae. The ascertainment of the appropriate signal sequence coding regions would be ascertainable based upon the particular lactic acid bacterial species that would be receiving the engineered cfaB, cfaA, cfaC, and cfaE structural gene sequence.

Lactic Acid Bacteria Benefits

There are several benefits to utilizing lactic acid bacteria to host and deliver the ETEC CFA/I fimbriae.

First, lactic acid bacteria do not present lipopolysaccharide complex (LPS) that is associated with the outer membrane of the *Salmonella* based vector.

Second, lactic acid bacteria do not present a problem with reversion to a virulent state, because lactic acid bacteria have a Generally Recognized as Safe (GRAS) status. GRAS status is a Food and Drug Administration designation that a chemical or substance added to food is considered safe by experts, and thus is exempted from the usual Federal Food, Drug, and Cosmetic Act food additive tolerance requirements.

Third, there is an insignificant risk of horizontal gene transfer to other invasive bacteria as would be more prevalent with a Gram-negative *Salmonella* vector.

Furthermore, the taught lactic acid bacteria vectors offer several distinct advantages over a *Salmonella* vector.

For instance, lactic acid bacteria have a long history of beneficial association with human intestinal microflora. Thus, the use of lactic acid bacteria offer the opportunity to create synergistic effects between recombinant lactic acid bacteria expressing ETEC CFA/I fimbriae and other resident intestinal microbial flora.

Consider that probiotics are products aimed at delivering living, potentially beneficial, bacterial cells to the intestinal ecosystem of humans and other animals. Strains of lactic acid bacteria are the most common microbes employed as probiotics. (Sonomoto, 2011). This presents the opportunity to utilize the taught lactic acid bacteria expressing ETEC CFA/I fimbriae in compositions that also comprise probiotic bacterial strains such as those from the genus *Lactobacillus* and *Bifidobacterium.*

As will be illustrated in the disclosed Examples, the present recombinant *Lactococcus lactis* strains expressing ETEC CFA/I fimbriae also demonstrate increased potency, as compared to the effects observed with *Salmonella* based delivery systems.

Therefore, the taught recombinant lactic acid bacterial vector system demonstrates unexpectedly superior properties, as compared to the previous *Salmonella* based delivery system. One notable property that will be elaborated upon in the Examples is the fact that the *Salmonella* based delivery system elicits a tremendous anti-CFA/I fimbriae immune response, as compared to the negligible immune response of the taught recombinant lactic acid bacterial system. These results suggest that the taught recombinant lactic acid bacteria expressing CFA/I fimbriae can be administered multiple times.

Enterotoxigenic *Escherichia coli* Colonization Factor Antigen I Fimbriae

Enterotoxigenic *Escherichia coli* (ETEC) use surface fimbriae (alternatively called pili) to attach to host tissues, an early and vital step in pathogenesis. (Qadri, 2005). At least 22 different types of antigenically distinct fimbrial CFAs have been identified among ETEC strains. One of the most commonly identified antigenic types identified in humans is colonization factor antigen I (CFA/I) fimbriae, which represent the archetype of class 5 fimbriae, the largest class of human-specific ETEC colonization factors. (Low, 1996). A 4-gene operon for fimbriae-related proteins is shared by all class 5 fimbriae. (Soto, 1999).

CFA/I fimbriae are under the control of an off-site positive regulator, cfaR, and are encoded by an operon containing 4 structural genes, cfaA, cfaB, cfaC, cfaE. It has been shown that expression of CFA/I fimbriae can be achieved in the absence of the cfaR positive regulator. (Wu, 1995).

The sequence of the native cfaI operon can be found at GenBank Accession No. M55661, which is hereby incorporated by reference in its entirety for all purposes.

cfaB encodes for the most abundant or major subunit of the fimbriae. cfaA encodes for a chaperone that plays a major role in the proper folding and assembling of the fimbriae. cfaC encodes for an usher protein, but it is also required for subsequent interaction for assembly of the fimbriae on the outer membrane surface. Finally, cfaE encodes for the tip-residing minor subunit.

Recent work has indicated that the protein encoded for by cfaE is the critical binding protein acting as an adhesin. (Baker, 2009).

Mature CFA/I fimbriae are a polymer typically consisting of >1000 copies of the major subunit CfaB, and 1 or a few copies of the adhesin CfaE.

As CfaE is present on CFA/I fimbriae at very low copy numbers, it is not detected in Western blots using antifimbriae antibody. (Sakellaris, 1996). Instead, the CfaB subunit is the predominant protein observed in Western blots and is used as a marker for translation of CFA/I operon proteins in general, in this case as a proxy for expression of CfaE.

Expression of Enterotoxigenic *E. coli* CFA/I Fimbriae in Gram-positive Bacteria The present disclosure teaches that Gram-positive bacteria expressing ETEC CFA/I fimbriae are therapeutically effective at treating or preventing autoimmune and/or inflammatory disease.

The method of expressing ETEC CFA/I fimbriae in Gram-positive bacteria may comprise inserting a plasmid carrying an engineered cfaI operon into a recipient Gram-positive bacterial host.

Further, in some embodiments, the method of expressing ETEC CFA/I fimbriae in Gram-positive bacteria may comprise stably integrating an engineered cfaI operon into the chromosome of a recipient Gram-positive bacterial host.

The term "plasmid" is used to refer to a molecule capable of autonomous replication that is suitable for transformation of a recipient bacterial strain and contains DNA sequences that direct and/or control the expression of inserted heterologous DNA sequences. Various types of plasmids may be used such as low and high copy number plasmids, narrow and broad-host range plasmids, expression plasmids, and cosmids.

In order to prevent loss of the plasmid expressing the heterologous CFA/I, an element may be added to the plasmid which enhances its stability. It is generally the case that the plasmids found in ETEC strains encoding the various colonization factor antigens are low copy number and stable enough to ensure their maintenance over many generations in the absence of specific selection mechanisms. However, following manipulation of these plasmids, these stable properties might be impaired. This problem may be alleviated by employing methods for improvement of plasmid stability, as would be known to those in the art.

In general, heterologous gene expression is achieved by cloning of the heterologous genes into the previously discussed plasmids, which are replicated within the recipient in multiple copies thus leading to high expression of foreign gene product. Expression of the taught heterologous sequences encoding E. coli CFA/I fimbriae are achievable by application of known genetic engineering techniques such as those described in, e.g. Sambrook and Russell (2001) "Molecular Cloning: A Laboratory Manual (3rd edition), Cold Spring Harbor Laboratory, Cold Spring Harbor Laboratory Press, New York, the entire contents of which are hereby incorporated by reference in their entirety for all purposes. As aforementioned, it has been demonstrated in the art that ETEC CFA/I fimbriae may be expressed in Gram-negative bacteria. For example, U.S. Pat. No. 7,759,106 and U.S. Pat. No. 7,943,122, the contents of each of which are hereby incorporated by reference, teach expression of ETEC CFA/I fimbriae in attenuated Gram-negative bacterial strains.

The disclosed engineered DNA construct, i.e. cfaI operon, comprising a promoter operably linked to DNA encoding the heterologous CFA/I fimbriae may be made and transformed into the Gram-positive bacteria using conventional techniques. Transformants containing the DNA construct may be selected, for example, by screening for a selectable marker on the construct. Bacteria containing the construct may be grown in vitro before being formulated for administration to the host. Selectable markers suitable for the taught recombinant bacteria would be known to those of skill in the art.

The recombinant bacteria taught herein may comprise nucleotide sequences encoding CFA/I fimbriae that have been codon optimized. "Codon optimization" is defined as modifying a nucleic acid sequence for enhanced expression in the cells of the host bacterial species of interest, e.g. Gram-positive bacteria, by replacing at least one, more than one, or a significant number of codons of the native ETEC CFA/I fimbriae sequence with codons that are more frequently or most frequently used in the genes of the recipient Gram-positive bacteria.

Various bacterial species exhibit particular bias for certain codons of a particular amino acid and thus codon optimization can ensure optimal expression of the ETEC CFA/I fimbriae in the recipient bacterial host cell being transformed. Codon preference or codon bias, is afforded by degeneracy of the genetic code, and is well documented among many organisms. Codon bias often correlates with the efficiency of translation of messenger RNA (mRNA), which is in turn believed to be dependent on, inter alia, the properties of the codons being translated and the availability of particular transfer RNA (tRNA) molecules. The predominance of selected tRNAs in a cell is generally a reflection of the codons used most frequently in peptide synthesis. Accordingly, the presently disclosed cfaA, cfaB, cfaC, and cfaE genes can be tailored for optimal gene expression in a given Gram-positive bacteria based on codon optimization.

Composition Formulation

The compositions presented herein are suitable for combination with any known pharmaceutically acceptable carrier, buffer, excipient, adjuvant, or mixture thereof.

Pharmaceutically acceptable carriers are well known and are usually liquids, in which an active therapeutic agent is formulated. In the present case, the active therapeutic agent is the disclosed recombinant bacteria expressing CFA/I fimbriae. The carrier generally does not provide any pharmacological activity to the formulation, though it may provide chemical and/or biological stability, release characteristics, and the like. Exemplary formulations can be found, for example, in Alfonso R. Gennaro. Remington: The Science and Practice of Pharmacy, 20th Edition. Baltimore, Md.: Lippincott Williams & Wilkins, 2000, the entire contents of which are hereby incorporated by reference, and include, but are not limited to, saline, water, buffered water, dextrose and the like.

The compositions presented herein may in some embodiments be placed within foodstuffs, such as: beverages, dairy products, yogurts, fermented food products, and the like, as feasible and consumer friendly delivery vehicles.

The compositions taught herein may also be delivered in food supplements, such as: powdered compositions comprising the taught recombinant bacterial cells, encapsulated compositions comprising the taught recombinant bacterial cells, or any liquid formulation comprising the taught recombinant bacterial cells.

The compositions may comprise other therapeutically effective agents such as anti-inflammatory cytokines.

The compositions may comprise other bacterial species, such as those bacterial species commonly referred to as "probiotics." Furthermore, "prebiotics" may also be present in the taught compositions.

Probiotics are often defined as live microorganisms that when administered in adequate amounts confer health benefits to the host. The compositions of the present disclosure may comprise probiotic microorganisms in an amount sufficient to at least partially produce a health benefit.

Prebiotics are often defined as food substances that promote the growth of probiotics in the intestines. They are not broken down in the stomach and/or upper intestine or absorbed in the GI tract of the person ingesting them, but they are fermented by the gastrointestinal microflora and/or by probiotics. The prebiotics that may be used in accordance with the present disclosure are not particularly limited and include all food substances that promote the growth of probiotics in the intestines.

Thus, disclosed herein are probiotic compositions comprising recombinant lactic acid bacteria expressing ETEC CFA/I fimbriae. In certain aspects, the taught probiotic compositions support a healthy immune system. The taught probiotic compositions may also be used to supplement an individual's normal dietary regime.

Furthermore, in certain embodiments, the present disclosure teaches dietary supplements that comprise recombinant bacteria comprising nucleotide sequences encoding ETEC CFA/I fimbriae. In particular embodiments, the recombinant bacteria expresses the ETEC CFA/I fimbriae. In certain aspects, the taught dietary supplements support a healthy immune system. The dietary supplements may also be used to supplement an individual's normal dietary regime.

The present disclosure also teaches food additive compositions comprising recombinant bacteria comprising nucleotide sequences encoding ETEC CFA/I fimbriae. In particular embodiments, the recombinant Gram-positive bacteria expresses the ETEC CFA/I fimbriae.

In certain aspects, the taught food additives support a healthy immune system.

The taught food additive compositions of the disclosure may be directly ingested or used as an additive in conjunction with foods.

It will be appreciated that the disclosed food additives may be incorporated into a variety of foods and beverages including, but not limited to: yogurt, ice cream, cheese, baked products such as bread, biscuits and cakes, dairy and dairy substitute foods, confectionery products, edible oil compositions, spreads, breakfast cereals, juices and the like.

Routes of Administration

The taught compositions may be used for parenteral administration, such as subcutaneous, intradermal, intramuscular, and intraperitoneal.

Particular embodiments of administration include oral administration.

Further embodiments include nasal delivery.

In some oral administration embodiments, the compositions comprise the disclosed recombinant bacteria expressing ETEC CFA/I fimbriae and optionally other molecules that are dissolved or suspended in a pharmaceutically acceptable, preferably an aqueous carrier. In addition, the composition may contain excipients, such as buffers, binding agents, diluents, flavors, lubricants, etc.

Quantitative Administration

The compositions taught herein may comprise varying amounts of the recombinant bacteria expressing ETEC CFA/I fimbriae. The particular amount of therapeutic bacterial vector present in the composition may depend upon the disease being treated and/or the subject being administered the therapeutic composition.

For instance, factors such as age, gender, ethnicity, genetic disposition to disease, health, weight, etc. may govern the amount of recombinant bacteria present in a composition.

The type of disease or condition being treated may also be taken into consideration when determining the optimal amount of recombinant bacterial vector that should be in a given composition.

In some embodiments, a particular amount of the disclosed therapeutic composition comprising recombinant bacterial cells expressing ETEC CFA/I fimbriae is defined as "a therapeutically effective amount" or "therapeutically effective dose." This amount represents a quantity of the disclosed compositions that is capable of eliciting an immune response in the recipient. For example, a "therapeutically effective dose" may be capable of increasing the level of an anti-inflammatory cytokine in the recipient. Furthermore, a "therapeutically effective does" may be able to suppress the level of an inflammatory cytokine in the recipient.

In some particular embodiments, a "therapeutically effective dose" increases the level of a regulatory cytokine selected from IL-10 or TGF-β in a subject upon administration of the taught composition, as compared to the level of the regulatory cytokine IL-10 or TGF-β present in the subject before administration of the taught composition.

In other embodiments, a "therapeutically effective dose" suppresses the level of at least one cytokine selected from the group consisting of IFN-γ, TNF-α, and IL-17 upon administration of the taught composition, as compared to the level of at least one of the cytokines selected from the group consisting of IFN-γ, TNF-α, and IL-17 present in the subject before administration of the taught composition.

Compositions of the present disclosure may comprise: $1\times10^8$ CFU, $2\times10^8$ CFU, $3\times10^8$ CFU, $4\times10^8$ CFU, $5\times10^8$ CFU, $6\times10^8$ CFU, $7\times10^8$ CFU, $8\times10^8$ CFUs, $9\times10^8$ CFU, $10\times10^8$ CFU, $11\times10^8$ CFU, $12\times10^8$ CFU, $13\times10^8$ CFU, $14\times10^8$ CFU, $15\times10^8$ CFU, $16\times10^8$ CFU, $17\times10^8$ CFU, $18\times10^8$ CFUs, $19\times10^8$ CFU, $20\times10^8$ CFU, $30\times10^8$ CFU, $40\times10^8$ CFU, $50\times10^8$ CFU, or more of the recombinant bacteria expressing CFA/I fimbriae.

Further, the compositions may comprise any range of CFU that is achievable based upon the aforementioned individual concentrations. For example, the compositions may comprise from $1\times10^8$ CFU to $50\times10^8$ CFU per treatment.

Further, the compositions may comprise ranges of: $1\times10^6$ to $1\times10^{10}$ CFU, or $1\times10^6$ to $2\times10^{10}$ CFU, or $1\times10^6$ to $3\times10^{10}$ CFU, or $1\times10^6$ to $4\times10^{10}$ CFU, or $1\times10^6$ to $5\times10^{10}$ CFU, or $1\times10^6$ to $6\times10^{10}$ CFU, or $1\times10^6$ to $7\times10^{10}$ CFU, or $1\times10^6$ to $8\times10^{10}$ CFU, or $1\times10^6$ to $9\times10^{10}$ CFU, or $1\times10^6$ to $10\times10^{10}$ CFU.

The compositions may comprise at least $1\times10^8$ CFU, or at least $2\times10^8$ CFU, or at least $3\times10^8$ CFU, or at least $4\times10^8$ CFU, or at least $5\times10^8$ CFU, or at least $6\times10^8$ CFU, or at least $7\times10^8$ CFU, or at least $8\times10^8$ CFUs, or at least $9\times10^8$ CFU, or at least $10\times10^8$ CFU, or at least $11\times10^8$ CFU, or at least $12\times10^8$ CFU, or at least $13\times10^8$ CFU, or at least $14\times10^8$ CFU, or at least $15\times10^8$ CFU, or at least $16\times10^8$ CFU, or at least $17\times10^8$ CFU, or at least $18\times10^8$ CFUs, or at least $19\times10^8$ CFU, or at least $20\times10^8$ CFU, or at least $30\times10^8$ CFU, or at least $40\times10^8$ CFU, or at least $50\times10^8$ CFU.

In a particular embodiment, the composition comprises approximately $5\times10^8$ CFU.

In some embodiments, the compositions comprise from $1\times10^6$ to $10\times10^{10}$ CFU, or $1\times10^6$ to $5\times10^{10}$ CFU.

The compositions may be administered once a day, twice a day, three times a day, four times a day, or five times a day to a subject in need of such treatment.

The compositions may also be administered at least once a day, at least twice a day, at least three times a day, at least four times a day, or at least five times a day.

Furthermore, the compositions may be administered on an as needed basis based upon a subject's physiological symptoms, such as pain, swelling, irritation or discomfort.

Some embodiments comprise administering the taught compositions comprising the recombinant bacteria on a prophylactic bases to a subject that does not presently experience physiological symptoms associated with an autoimmune or inflammatory disease.

In particular embodiments, the compositions may be taken daily as part of a food product delivery vehicle, e.g. yogurt, as part of a daily health regimen.

Collagen Induced Arthritis (CIA) Model

Collagen induced arthritis (CIA), a model of rheumatoid arthritis (RA), can be induced upon immunization with heterologous collagen II (CII) in DBA/1 or C57BL/6 mice or by mAbs to CII combined with LPS. CIA shares with RA several critical characteristics of the disease pathogenesis, including $CD4^+$ T cells' mediated inflammation and extensive cartilage and bone damage, resulting in joint deformities. This similarity permits the use of the CIA model as an investigative tool to test novel approaches for prevention and treatment of RA. (Courtenay, 1980; Terato, 1992; Terato 1995).

Experimental Autoimmune Encephalomyelitis

Experimental autoimmune encephalomyelitis (EAE) is the most commonly used experimental model for the human inflammatory demyelinating disease, multiple sclerosis (MS). EAE is a complex condition in which the interaction between a variety of immunopathological and neuropathological mechanisms leads to an approximation of the key pathological features of MS: inflammation, demyelination, axonal loss and gliosis. The counter-regulatory mechanisms of resolution of inflammation and remyelination also occur in EAE, which, therefore can also serve as a model for these processes. Moreover, EAE is often used as a model of cell-mediated organ-specific autoimmune conditions in general. (Constantinescu, 2011).

EXAMPLES

I. Expression of *E. coli* CFA/I Fimbriae in *Lactococcus* for Treatment of Arthritis Recombinant *Lactococcus lactis* expressing ETEC CFA/I fimbriae, when orally delivered to mice, is able to prevent the symptoms and to block the progression of collagen-induced arthritis.

Construction of *Lactococcus*-CFA/I Vector

*Lactococcus lactis* was selected as the bacterial species to carry the ETEC CFA/I operon. The *E. coli* cfaI operon was rebuilt to enable expression in the Gram-positive *Lactococcus lactis* bacteria. The native cfaI operon was modified in several ways.

First, each of the 4 structural genes of the cfaI operon, i.e. cfaA, cfaB, cfaC, and cfaE, were modified from the native gene sequence to include Gram-positive signal sequence coding regions. The signal sequence coding regions encode for *Lactococcus* compatible signal peptides, which are alternatively referred to as leader sequences or leader peptides. Thus, the native signal sequence coding regions were removed and replaced with signal sequences compatible with *Lactococcus*. The signal sequence usp45 from *Lactococcus lactis* subs. *cremoris* was used with cfaB. The signal sequence Exp4 from *Lactococcus lactis* subs. *cremoris* was used with cfaA. The signal sequence lac from *Lactococcus lactis* subs. *cremoris* was used with cfaC. The signal sequence prtP from *Lactococcus lactis* subs. *cremoris* was used with cfaE.

Second, the native order of the structural genes present in the cfaI operon—as can be found at GenBank Accession No. M55661—was altered. The normal order of the structural genes in the cfaI operon is: cfaA, cfaB, cfaC, and cfaE. However, in the present disclosure, the inventors have engineered the structural genes to be in the following order: cfaB, cfaA, cfaC, and cfaE.

Third, the native cfaI operon was further altered by removing untranslated *E. coli* sequences.

Fourth, the introduction of Shine-Dalgarno sequences to enable protein translation from the upstream promoter. The Shine-Dalgarno sequences used were AGGAGG.

The entire engineered cfaB, cfaA, cfaC, and cfaE gene sequence along with the associated signal sequence coding regions and below discussed promoters can be found in SEQ ID NO: 1. Further, the individual structural genes with associated signal sequence coding regions are as follows: cfaB (SEQ ID NO: 2), cfaA (SEQ ID NO: 3), cfaC (SEQ ID NO: 4), and cfaE (SEQ ID NO: 5). The encoded peptide sequences, corresponding to the aforementioned gene sequences, with associated and translated peptide leader sequences are as follows: CfaB (SEQ ID NO: 9), CfaA (SEQ ID NO: 10), CfaC (SEQ ID NO: 11), and CfaE (SEQ ID NO: 12).

Fifth, the engineered sequences cfaB, cfaA, cfaC, and cfaE were placed under the control of a lactic acid bacteria composite (tandem) promoter composed of nisin, P170, and CP25, each of which has been modified from its native sequence to enhance RNA stability. The promoter properties are as follows:

a) A nisin-inducible promoter originally resident in the pMSP3535H3 vector. This component, whether induced or not, was found to have no consequence in this composite configuration. The nisin promoter is found in SEQ ID NO: 6.

A particular embodiment of the disclosure does not include the nisin promoter.

b) The P170 is acid inducible, and has spurious ATG right after the TATA −10 box eliminated. 6+1 base pairs after −10 sequence modified for optimal consensus. It is followed by its own untranslated mRNA leader partially deleted to increase its activity. (Madsen, 1999). The P170 promoter is found in SEQ ID NO: 7.

In a particular embodiment, the P170 promoter is coupled to the below described CP25 promoter and the previously discussed nisin-inducible promoter is not utilized.

c) The CP25 promoter with spurious ATG in this latter promoter has been left because of how the promoter was designed and also because ATG is immediately followed by two framed stop codons. (Jensen, 1998). It is followed by slpA untranslated leader sequences (UTLs), which reportedly stabilize mRNA. (Narita, 2006). In this last section, ATGs have been left because of self annealing constraints and because it proved functional regardless of the presence of spurious ATGs. gg has been changed to create a Kpn1 site that will allow removal of the untranslated slpA leader as well as cloning the remaining promoter into the theta vector pIB184. The CP25 promoter is found in SEQ ID NO: 8.

Experimental Protocol

To enable future human testing and transient presence, *L. lactis* IL1403 (Lee, 2006; Steen, 2008) was selected to generate *L. lactis*-CFA/I by transforming it using the expression vector pMSP3535H3 with a nisin-inducible promoter. (Oddone, 2009).

Figure 3:
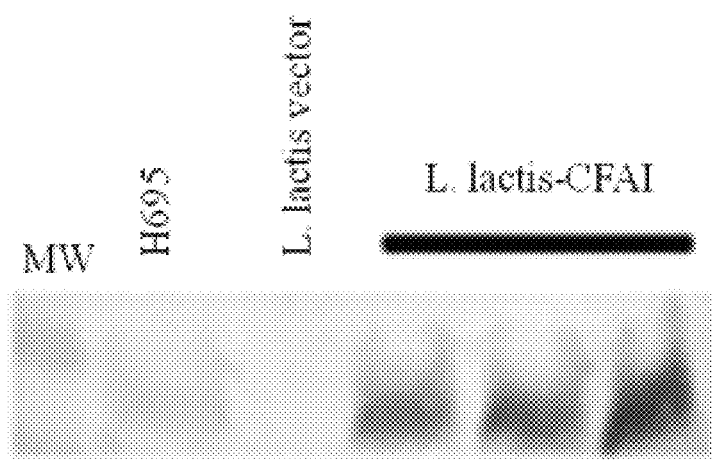
FIG. 3 illustrates the immunotherapeutic potential for *Lactococcus*-CFA/I, by identifying three clones thru Western blot analysis. These three clones were found to express similar, or more abundant, fimbriae than *E. coli*-CFA/I strain H695.

To assess the immunotherapeutic potential for *L. lactis*-CFA/I, three clones were identified by Western blot analysis and were found to express similar or more abundant fimbriae than *E. coli*-CFA/I (strain H695). (Wu, 1995). FIG. 3 illustrates this result.

Groups of B6 mice were induced with CIA and treated upon disease onset with PBS, *L. lactis* vector, or *L. lactis*-CFA/I, and a second treatment was given one week later. The *L. lactis* vector contained a plasmid without the engineered cfaI operon. The *L. lactis*-CFA/I contained the engineered cfaI operon pBzMM153.

Results

Figure 4:
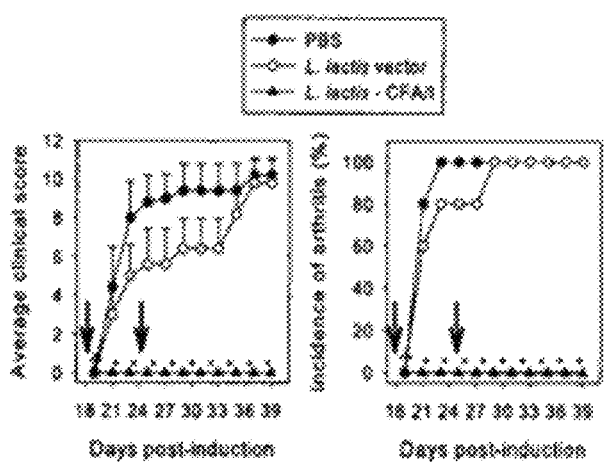
FIG. 4 illustrates that groups of B6 mice (n=5/group) were induced with CIA by being challenged with chick CII in complete Freund's adjuvant on day 0, and 18 days later at disease onset, mice were orally dosed with $5\times10^8$ CFUs of: (1) *L. lactis* vector (i.e. plasmid without engineered cfaI operon, depicted by open circles), (2) or with *L. lactis*-CFA/I (i.e. plasmid with engineered cfaI operon, depicted by filled triangles), (3) or with PBS (depicted by filled circles). A second dose of the aforementioned was given 1 week later. The dosings are depicted by black downward arrows. As illustrated in the figure, all *L. lactis*-CFA/I mice were completely protected; unlike *L. lactis* vector mice and PBS mice. The protection afforded by *L. lactis*-CFA/I mice is evidenced by the average clinical score measure on the left side of the left panel and the incidence of arthritis measure on the left side of the right panel.

The results of the CIA experiment are illustrated in FIG. 4.

*L. lactis*-CFA/I-treated mice showed no clinical disease, as demonstrated by the 0 average clinical score exhibited by mice treated with *L. lactis*-CFA/I. Compare this result to the significantly elevated average clinical scores exhibited by the PBS and *L. lactis* vector treated mice.

Further, *L. lactis*-CFA/I treated mice showed no incidence of disease, as demonstrated by the 0 incidence of arthritis score exhibited by mice treated with *L. lactis*-CFA/I. Compare this result to the significantly elevated incidence of arthritis scores exhibited by the PBS and *L. lactis* vector treated mice.

Histological examination of the mice tissues confirmed these findings.

Figure 5:
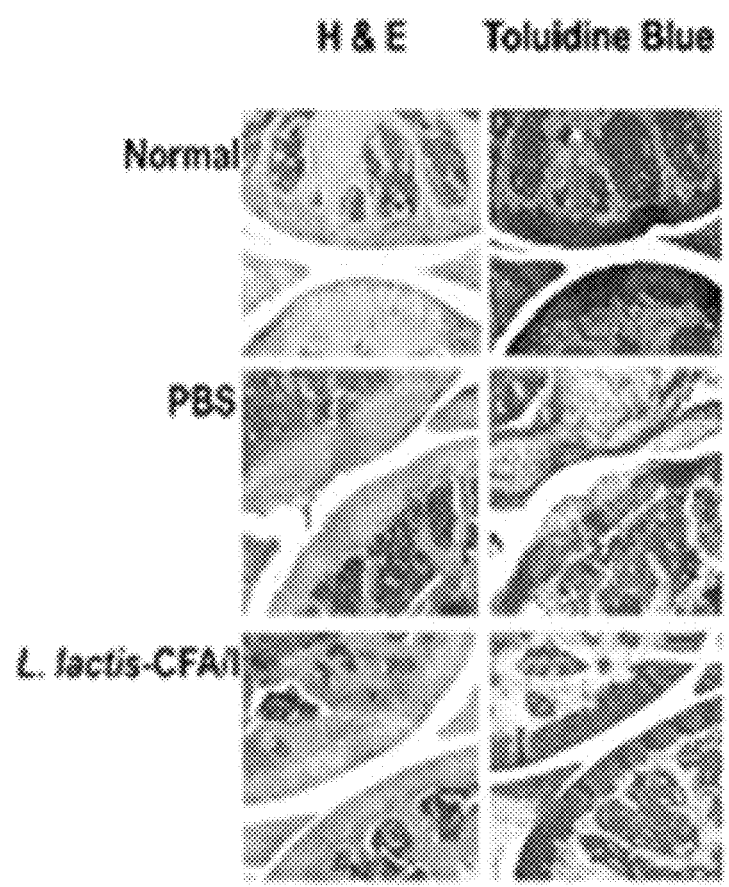
FIG. 5 illustrates a histological stain of treated mice tissue that shows *L. lactis*-CFA/I mice did not present evidence of clinical disease. Hematoxylin and eosin stain (H&E) are in the left column and toluidine blue stain is in the right column. The stainings were performed on joint sections from treated mice used in the experiment illustrated in FIG. 4. The *L. lactis*-CFA/I mice showed no damage to cartilage, and *L. lactis* vector mice showed similar pathology as PBS-treated mice (data not shown for *L. lactis* vector mice).

FIG. 5 depicts the histological results.

At the termination of the study, total peripheral lymph node (PLN) CD4$^+$ T cells were isolated and restimulated in vitro with CII, in the presence of irradiated splenic APCs, and secreted cytokines were measured by ELISA.

Figure 6:
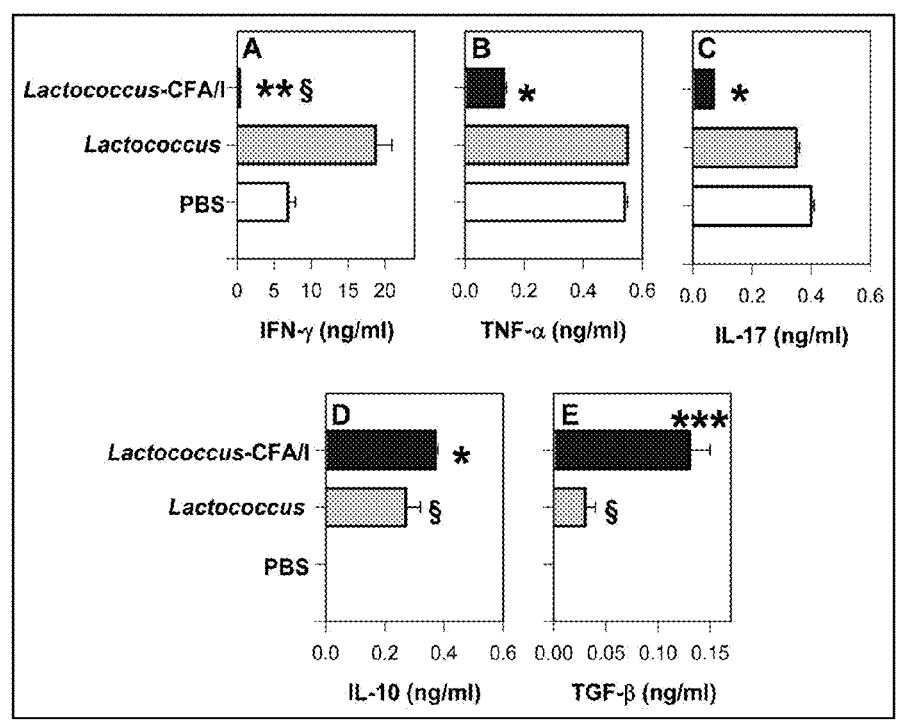
FIG. 6 illustrates that *L. lactis*-CFA/I induces IL-10 and TGF-β, while dampening proinflammatory cytokines Peripheral lymph node (PLN) CD4$^+$ T cells isolated from collagen-induced arthritis (CIA) mice treated with PBS, *L. lactis* vector, or *L. lactis*-CFA/I (from FIG. 4) were co-cultured with irradiated antigen-presenting cells (APCs) and stimulated with collagen II (CII) for 4 days. Supernatants were analyzed for (A) IFN-γ, (B) TNF-α, (C) IL-17, (D) IL-10, and (E) TGF-β production. *P<0.001, P<0.005, *P<0.05 versus PBS treated mice; $^§$P<0.015 versus *L. lactis*-CFA/I.

*L. lactis*-CFA/I suppressed IFN-γ, TNF-α, and IL-17 and stimulated the regulatory cytokines, IL-10 and TGF-β. These results are depicted in FIG. 6. *L. lactis* vector also produced the IL-10 and TGF-β cytokines, but was significantly different from *L. lactis*-CFA/I.

Thus, *L. lactis*-CFA/I is protective against CIA, showing greater potency than *Salmonella*-CFA/I or the *Lactococcus* vector containing a plasmid without the engineered cfaI operon pBzMM153.

II. *L. lactis*-CFA/I is Only Mildly Immunogenic Thus Allowing for Multiple Instillations The immunogenicity of the *L. lactis*-CFA/I was tested to determine if repeat doses would be feasible in a subject without the risk of eliciting a major negative immunogenic response.

Experimental Protocol

Mice were dosed twice, as described in Experiment I, with either: (a) *L. lactis* vector with a plasmid not containing the engineered cfaI operon pBzMM153, (b) *L. lactis*-CFA/I, or (c) *Salmonella*-CFA/I.

Results

The *Lactococcus* vector without the engineered CFA/I operon along with the *L. lactis*-CFA/I did not elicit serum IgG, IgG1, IgG2a, or IgG2b Ab titers to CFA/I fimbriae. See FIG. 7.

In contrast, *Salmonella*-CFA/I did elicit a significant immune response. See FIG. 7.

Figure 7:
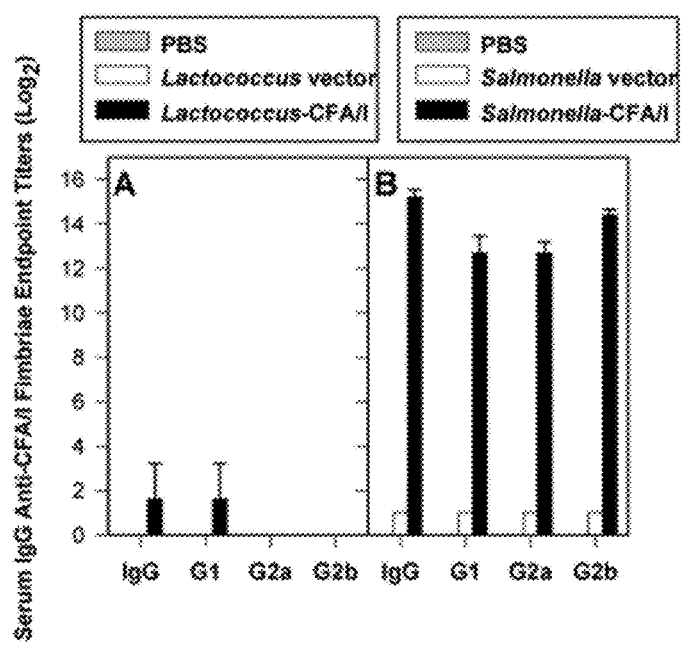
FIG. 7 illustrates that *L. lactis*-CFA/I does not induce anti-CFA/I fimbriae Abs. Mice dosed twice, as described in FIG. 4, with *L. lactis* vector or *L. lactis*-CFA/I, as illustrated in panel (A), did not elicit serum IgG, IgG1, IgG2a, or IgG2b Ab titers to CFA/I fimbriae. This is in stark contrast to the data illustrated in panel (B), demonstrating *Salmonella* vector and *Salmonella*-CFA/I, which did elicit significant anti-CFA/I fimbriae Abs. The data presented in this figure suggests that *L. lactis*-CFA/I does not stimulate Abs to fimbrial antigens and may allow repeated dosing.
Figure 8:
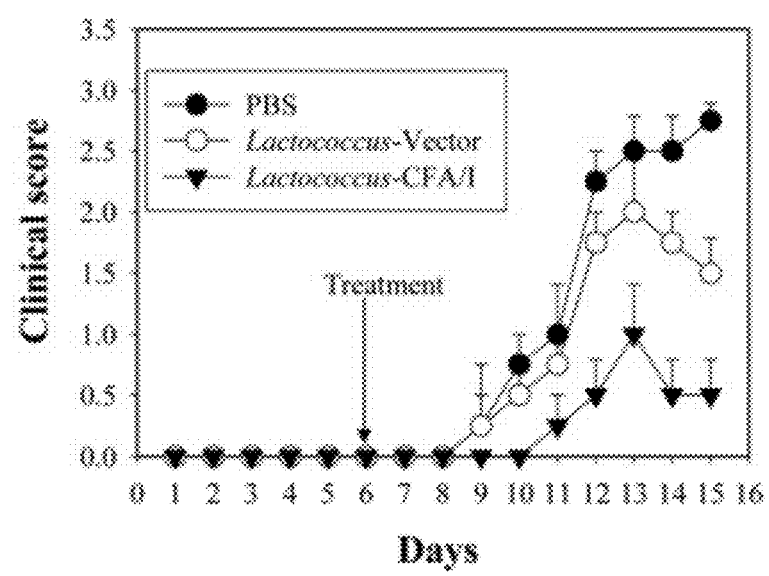
FIG. 8 illustrates that *L. lactis*-CFA/I confers protection against experimental autoimmune encephalomyelitis (EAE). C57BL/6 mice were induced with EAE on day 0 and treated orally with $5\times10^8$ CFUs of: *L. lactis* vector, *L. lactis*-CFA/I, or with PBS on day 6 post-challenge. Clinical scores were monitored until day 16.

The drastic serum IgG, IgG1, IgG2a, and IgG2b Ab titers elicited by the *Salmonella* vector expressing ETEC CFA/I fimbriae is demonstrated in Panel B of FIG. 7. The minimal response elicited by *Lactococcus* expressing ETEC CFA/I fimbriae is demonstrated in Panel A of FIG. 7.

These results suggest that *L. lactis*-CFA/I does not stimulate Abs to fimbrial Ags and may allow repeated dosing.

III. Expression of *E. coli* CFA/I Fimbriae in *Lactococcus* for Treatment of Experimental Autoimmune Encephalomyelitis Recombinant *Lactococcus lactis* expressing ETEC CFA/I fimbriae, when orally delivered to mice, is able to prevent the symptoms and to block the progression of Experimental Autoimmune Encephalomyelitis (EAE).

Construction of *L. lactis*-CFA/I Vector

*L. lactis*-CFA/I vector was constructed as outlined in Example I.

Experimental Protocol

To test its efficacy against EAE, C57L/6 mice were subjected to myelin oligodendrocyte glycoprotein (MOG)-induced EAE. (Jun, 2005; Ocho-Repáraz, 2007; Ocho-Repáraz, 2008).

On day 6 post-MOG peptide challenge, groups of mice were dosed orally with PBS or 5×10$^8$ CFUs of *L. lactis* vector or *L. lactis*-CFA/I.

Results

*L. lactis*-CFA/I-treated mice developed minimal disease, unlike groups treated with PBS or *L. lactis* vector (P<0.05).

This intervention also resulted in significant reductions in IL-17 and IFN-γ production via the stimulation of the anti-inflammatory cytokines, IL-10 and TGF-β.

Thus, the data provides further evidence that *L. lactis*-CFA/I, not *L. lactis* vector, mediates intervention upon EAE via the stimulation of anti-inflammatory cytokines.

IV. Electron Microscopy Verifies that ETEC CFA/I Fimbriae are Expressed in *L. lactis*

Figure 9:
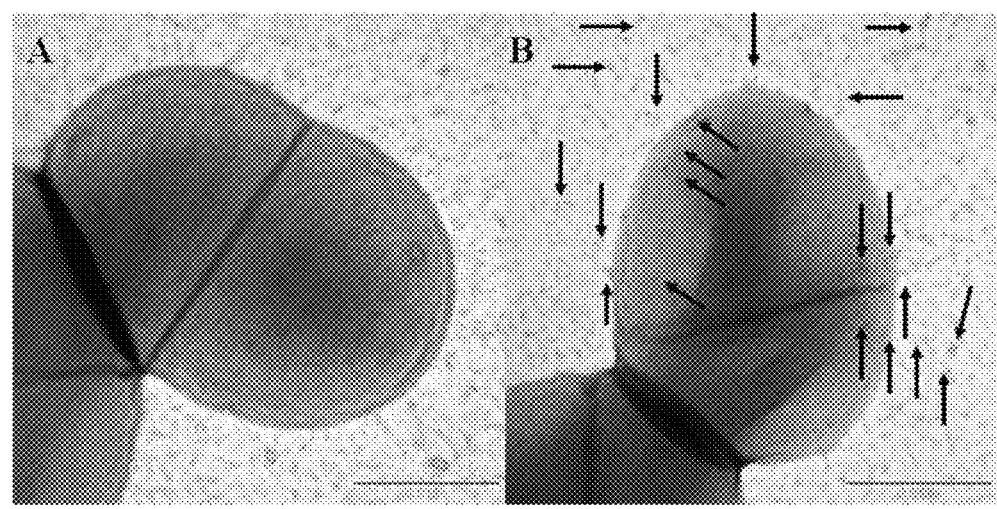
FIG. 9 illustrates an electron microscopy image of *Lactococcus* bacteria. Immunogold staining of *Lactococcus lactis* without the pBzMM153 operon of FIG. 1 is depicted in panel A. Immunogold staining of *Lactococcus lactis* containing the pBzMM153 operon of FIG. 1 is depicted in panel B. The Lactococci were stained with rabbit anti-CFA/I fimbriae antibody plus gold-labeled anti-rabbit IgG. The black arrows indicate labeled fimbriae and the sold black line at the bottom of the micrographs represents 0.5 μM.

EM images were taken of immunogold stained *Lactococcus lactis* without the pBzMM153 operon and *Lactococcus lactis* containing the pBzMM153 operon. FIG. 9 depicts the results of this experiment and illustrates that ETEC CFA/I fimbriae are expressed in the recombinant *L. lactis*-CFA/I bacteria.

V. *L. lactis*-CFAII Activates Human T$_{reg}$ Cells

Experimentation was performed to establish the capacity of *L. lactis*-CFA/I to augment human T$_{reg}$ cells. Human peripheral blood dendritic cells (DCs) were isolated from a normal donor and stimulated overnight with 5.0 μg/ml of recombinant *L. lactis*-CFA/I fimbriae, and then cultured for 4 days with autologous purified CD4$^+$ T cells. These were stimulated with anti-CD3 plus anti-CD28 mAbs, and the CD4$^+$ T cells were analyzed by flow cytometry for increased percentage of FOXP3$^+$ IL-10$^+$ T$_{reg}$ cells.

Figure 10:
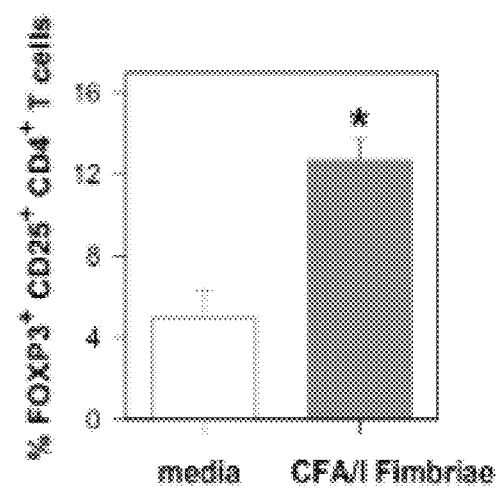
FIG. 10 illustrates that *L. lactis*-CFA/I fimbriae stimulate human $T_{reg}$ cell induction. Isolated normal human dentritic cells (DCs) stimulated with *L. lactis*-CFA/I overnight and cultured for 4 days with autologous purified CD4$^+$ T cells stimulated with anti-CD3 mAb+CFA/I showed 2.6-fold increase in $T_{reg}$ cells and a third of these were IL-10$^+$; *P=0.002 vs. media.

The results are illustrated in FIG. 10. The results demonstrate that *L. lactis*-CFA/I fimbriae were able to stimulate FOXP3$^+$ T$_{reg}$ cells by nearly 3-fold, and one-third of these T$_{reg}$ cells produced IL-10. Thus, these results demonstrate that human DCs and CD4$^+$ T cells are responsive to *L. lactis*-CFA/I fimbriae and mimic the murine results in driving and/or activating T$_{reg}$ cells to resolve autoimmune disease.

Experimental Observations

The present inventors have surprisingly been successful in manipulating the *E. coli* cfaI operon—that encodes ETEC CFA/I fimbriae—in such a way as to enable expression of the ETEC CFA/I fimbriae in *Lactoccous lactis* bacteria.

The successful derivation of the engineered operon pBzMM153 allows for the expression of ETEC CFA/I fimbriae in *Lactococcus lactis* bacteria.

The results demonstrate that recombiantly engineered *Lactococcus lactis* expressing ETEC CFA/I fimbriae can be used prophylactically and therapeutically to prevent or block the progression of human autoimmune disorders.

The present disclosure is a significant advancement in the art that heretofore had been reliant upon problematic *Salmonella* based fimbrial delivery vectors.

Despite major hurdles in the expression of an entire Gram-negative multi-gene operon into a Gram-positive microorganism, the present inventors have successfully achieved such a result.

The previously discussed clinical data were gathered with a double-blind approach, where the scorer was unaware of the experimental design. Experiments were repeated several times by different investigators, which produced identical results. The utilization of a GRAS microorganism, i.e. *Lactoccous lactis*, eliminates many of the toxicities associated with Gram-negative or *Salmonella* vaccine vectors.

The results demonstrate that the disclosed recombinant *Lactococcus lactis* expressing ETEC CFA/I fimbriae, when orally delivered to mice, is able to prevent the symptoms and to block the progression of collagen-induced arthritis. CIA is a model of rheumatoid arthritis and therefore implicates the ability of the recombinant bacteria taught herein to be an effective treatment for this highly pervasive autoimmune disease.

Further, the results demonstrate that the disclosed recombinant *Lactococcus lactis* expressing ETEC CFA/I fimbriae, when orally delivered to mice, is able to prevent the symptoms and to block the progression of experimental autoimmune encephalomyelitis. EAE is a model for multiple sclerosis and therefore implicates the ability of the recombinant bacteria taught herein to be an effective treatment for this autoimmune disease.

Further, the data demonstrates that *L. lactis* expressing ETEC CFA/I fimbriae activates human $T_{reg}$ cells.

Thus, the present inventors have illustrated that the recombinant *Lactococcus lactis* expressing ETEC CFA/I fimbriae have strong potential to act as multi-purpose modulators of pathological immune response in absence of an autoantigen.

Although it is unclear whether the CFA/I fimbriae are fully assembled on the cell surface of the *Lactococcus*, it is the delivery of the fimbriae to the mucosa, whether fully assembled or unassembled, which likely results in protection against autoimmune insult.

The experimental data also suggests that both components of the secreted fimbrial proteins, CfaB and CfaE are required for immunogenic protection. Without wishing to be bound to a particular theory, the inventors surmise that this could account for why the unassembled fimbriae can confer protection against autoimmune disease.

An added benefit of the present recombinant *Lactococcus lactis* is that the vector is not very immunogenic. This property of the disclosed recombinant bacteria thus allows for multiple instillations/doses of a therapeutic composition comprising the recombinant bacteria if required.

The data illustrates that protection against autoimmune disease—as represented by the CIA and EAE mice models—can be achieved with two doses of the recombinant *Lactococcus lactis* expressing ETEC CFA/I fimbriae. The amount of recombinant vector required may be dependent upon the type of disease.

In conclusion, the inventors have disclosed a novel GRAS-based therapeutic that can be administered mucosally, e.g., orally, nasally, or sublingually, to treat autoimmune diseases such as arthritis, multiple sclerosis, colitis, diabetes, etc.

For oral delivery, the recombinant *Lactococcus lactis* ETEC CFA/I fimbrial vector can be used in the preparation of fermented foods, e.g., yogurt, as one feasible delivery instrument.

Given the *Lactococcus lactis* ETEC CFA/I fimbrial vector's minimal immunogenicity, it can be delivered multiple times as an intervention and possibly be used to enhance conventional drug treatments or, possibly, eliminating their use all together.

REFERENCES

1. Kochetkova, I., Trunkle, T., Callis, G., Pascual, D. W., 2008, Vaccination Without Autoantigen Protects Against Collagen II-Induced Arthritis via Immune Deviation and Regulatory T Cells, *J. of Immunology*, 181:2741-2452.
2. Scott, D. L., Wolfe, F., Huizinga, T. W., 2010, Rheumatoid arthritis, *Lancet*, 376 (9746): 1094-1108.
3. Lozano, L. R., Naghavi, M., Foreman, K., Lim, S., Shibuya, K., Aboyans, V., Abraham, J., Adair, T. et al., 2012, Global and regional mortality from 235 causes of death for 20 age groups in 1990 and 2010: a systematic analysis for the Global Burden of Disease Study 2010, *Lancet*, 380 (9859):2095-2128.
4. Attridge, S. R., Davies, R., LaBrooy, J. T., 1997, Oral delivery of foreign antigens by attenuated *Salmonella*: consequences of prior exposure to the vector strain, *Vaccine*, 15 (2):155-162.
5. Detmer, A., Glenting, J., 2006, Live bacterial vaccines—a review and identification of potential hazards, *Microbial Cell Factories*, 5:23, 1-12.
6. Sonomoto, K., Yokota, A., 2011, Lactic Acid Bacteria and Bifidobacteria: Current Progress in Advanced Research. Caister Academic Press. ISBN 978-1-904455-82-0.
7. Qadri, F., Svennerholm, A. M., Faruque, A. S., Sack, R. B., 2005, Enterotoxigenic *Escherichia coli* in developing countries: Epidemiology, microbiology, clinical features, treatment, and prevention, *Clin Microbiol Rev*, 18:465-483.
8. Low, D., Braaten, B., Van der Woude, M., 1996, Fimbriae in *Escherichia coli* and *Salmonella*: Cellular and Molecular Biology, eds. Neidhart F. C., et al., Am. Soc. Microbiol., Washington, D.C., Vol 2, pp 146-157.
9. Soto, G. E., Hultgren, S. J., 1999, Bacterial adhesins: Common themes and variations in architecture and assembly, *J Bacteriol*, 181:1059-1071.
10. Wu, S., Pascual D. W., VanCott, J. L., McGhee, J. R., Maneval, D. R. Jr., Levine, M. M., and Hone, D. M., 1995, Immune response to *Escherichia coli* and *Salmonella typhimurium* vectors that express colonization factor antigen I (CFA/I) of enterotoxigenic *E. coli* (ETEC) in the absence of the CFA/I positive regulator cfaR., *Infect. Immun.*, 63:4933-4938.
11. Baker, K. K., Levine, M. M., Morison, J., Phillips, A., Barry, E. M., 2009, CfaE tip mutations in enterotoxigenic *Escherichia coli* CFA/I fimbriae define critical human intestinal binding sites, *Cell Microbiology*, 11 (5):742-754.
12. Sakellaris, H., Balding, D. P., Scott, J. R., 1996, Assembly proteins of CS1 pili of enterotoxigenic *Escherichia coli*, *Mol Microbiol.*, 21:529-541.
13. Courtenay, J. S., Dallman, M. J., Dayan, A. D., Martin, A., Mosedale, B., 1980, Immunization against heterologous type II collagen induces arthritis in mice, *Nature*, 283: 666-668.
14. Terato, K., Hasty, K. A., Reife, R. A., Cremer, M. A., Kang, A. H., Stuart, J. M., 1992, Induction of arthritis with monoclonal antibodies to collagen, *J. Immunol.*, 148: 2103-2108.
15. Terato, K., Haeper, D. S., Griffiths, M. M., Hasty, D. L., Ye, X. J., Cremer, M. A., Seyer, J. M., 1995, Collagen-induced arthritis in mice: synergistic effect of *E. coli* lipopolysaccharide bypasses epitope specificity in the induction of arthritis with monoclonal antibodies to type II collagen, *Autoimmun*, 22: 137-147.
16. Constantinescu, C. S., Farooqi, N., O'Brien, K., Gran, B., 2011, Experimental autoimmune encephalomyelitis (EAE) as a model for multiple sclerosis (MS), *Br J Pharmacol.*, 164 (4):1079-106.
17. Madsen, S. M., Arnau, J., Vrang, A., Givskov, M., and Israelsen, H., 1999, Molecular characterization of the pH-inducible and growth phase-dependent promoter P170 of *Lactococcus lactis.*, *Mol. Microbiol.*, 32:75-87.

18. Jensen, P. R. and Hammer, K., 1998, The sequence of spacers between the consensus sequences modulates the strength of prokaryotic promoters, *Appl. Environ. Microbiol.*, 64:82-87.

19. Narita, J., Ishida, S., Okano, K., Kimura, S., Fukuda, H., and Kondo, A., 2006, Improvement of protein production in lactic acid bacteria using 5'-untranslated leader sequence of slpA from *Lactobacillus acidophilus*, Improvement in protein production using UTLS, *Appl. Microbiol. Biotechnol.*, 73:366-373.

20. Lee, P. and Faubert, G. M., 2006, Oral immunization of BALB/c mice by intragastric delivery of *Streptococcus gordonii*—expressing Giardia cyst wall protein 2 decreases cyst shedding in challenged mice, *FEMS Microbiol. Lett.*, 265:225-236.

21. Steen, A., Buist, G., Kramer, N. E., Jalving, R., Benus, G. F., Venema, G., Kuipers, O. P, and Kok, J., 2008, Reduced lysis upon growth of *Lactococcus lactis* on galactose is a consequence of decreased binding of the autolysin AcmA, *Appl. Environ. Microbiol.*, 74:4671-4679.

22. Oddone, G. M., Mills, D. A., and Block, D. E., 2009, Incorporation of nisI-mediated nisin immunity improves vector-based nisin-controlled gene expression in lactic acid bacteria, *Plasmid*, 61:151-158.

23. Jun, S., Gilmore, W., Callis, G., Rynda, A., Haddad, A., and Pascual, D. W., 2005, A live diarrheal vaccine imprints a Th2 cell bias and acts as an anti-inflammatory vaccine, *J. Immunol.*, 175:6733-6740.

24. Ochoa-Repáraz, J., Riccardi, C., Rynda, A., Jun, S., Callis, G., and Pascual, D. W., 2007, Regulatory T cell vaccination without autoantigen protects against experimental autoimmune encephalomyelitis, *J. Immunol.*, 178:1791-1799.

25. Ochoa-Repáraz, J., Rynda, A., Ascón, M. A., Yang, X., Kochetkova, I., Riccardi, C., Callis, G., Trunkle, T., and Pascual, D. W., 2008, IL-13 production by regulatory T cells protects against experimental autoimmune encephalomyelitis independently of autoantigen, *J. Immunol.*, 181:954-968.

What is claimed is:

1. A composition for the treatment of an autoimmune or inflammatory disease, the composition comprising:
a recombinant *Lactococcus lactis* bacterial cell comprising a nucleotide sequence coding for enterotoxigenic *Escherichia coli* colonization factor antigen I fimbriae genes cfaA, cfaB, cfaC, and cfaE, wherein the bacterial cell expresses *E. coli* colonization factor antigen 1 fimbriae genes cfaA, cfaB, cfaC, and cfaE; and wherein the cfaA gene comprises SEQ ID NO: 3, the cfaB gene comprises SEQ ID NO: 2, the cfaC gene comprises SEQ ID NO: 4, and the cfaE gene comprises SEQ ID NO: 5, and an acceptable carrier.

2. The composition of claim 1, wherein the composition induces an anti-inflammatory response in a subject treated with the composition.

3. The composition of claim 1, wherein said *E. coli* colonization factor antigen I fimbriae genes are oriented in a nucleotide sequence operon in the following non-native order: cfaB, cfaA, cfaC, and cfaE.

4. The composition of claim 1, wherein the nucleotide sequence is operably linked to a composite promoter.

5. The composition of claim 4, wherein the composite promoter comprises an inducible promoter.

6. The composition of claim 1, wherein the nucleotide sequence is operably linked to a composite promoter comprising at least one sequence selected from the group consisting of: SEQ ID NO:6, SEQ ID NO:7, and SEQ ID NO:8.

7. The composition of claim 1, wherein the nucleotide sequence is operably linked to a composite promoter comprising SEQ ID NO:6, SEQ ID NO:7, and SEQ ID NO:8.

8. A method comprising administering to a subject the composition of claim 1.

9. The method of claim 8, wherein the composition administered increases the level of a regulatory cytokine selected from IL-10 or TGF-β in the subject as compared to the level of the regulatory cytokine IL-10 or TGF-β present in the subject before said administering.

10. The method of claim 8, wherein the composition administered decreases the level of at least one cytokine selected from the group consisting of IFN-γ, TNF-α, and IL-17 as compared to the level of at least one of the cytokines selected from the group consisting of IFN-γ, TNF-α, and IL-17 present in the subject before said administering.

11. A composition for the treatment of an autoimmune or inflammatory disease, the composition comprising:
a recombinant *Lactococcus lactis* bacterial cell comprising a nucleotide sequence coding for enterotoxigenic *Escherichia coli* colonization factor antigen I fimbriae genes cfaA, cfaB, cfaC, and cfaE, wherein the bacterial cell expresses *E. coli* colonization factor antigen 1 fimbriae genes cfaA, cfaB, cfaC, and cfaE; and wherein the nucleotide sequence comprises a polynucleotide sequence sharing at least 95% sequence identity with SEQ ID NO: 1, and an acceptable carrier.

12. The composition of claim 11, wherein the polynucleotide sequence shares 100% sequence identity with SEQ ID NO:1.

13. A recombinant *Lactococcus lactis* bacterial cell comprising a nucleotide sequence coding for enterotoxigenic *Escherichia coli* colonization factor antigen I fimbriae genes cfaA, cfaB, cfaC, and cfaE, wherein the bacterial cell expresses *E. coli* colonization factor antigen I fimbriae genes comprising cfaA, cfaB, cfaC, and cfaE; and wherein the cfaA gene comprises SEQ ID NO: 3, the cfaB gene comprises SEQ ID NO: 2, the cfaC gene comprises SEQ ID NO: 4, and the cfaE gene comprises SEQ ID NO: 5.

14. The recombinant *Lactococcus lactis* bacterial cell of claim 13, wherein said *E. coli* colonization factor antigen I fimbriae genes are oriented in a nucleotide sequence operon in the following non-native order: cfaB, cfaA, cfaC, and cfaE.

15. The recombinant *Lactococcus lactis* bacterial cell of claim 13, wherein the nucleotide sequence is operably linked to a composite promoter.

16. The recombinant *Lactococcus lactis* bacterial cell of claim 15, wherein the composite promoter comprises an inducible promoter.

17. The recombinant *Lactococcus lactis* bacterial cell of claim 13, wherein the nucleotide sequence is operably linked to a composite promoter comprising at least one sequence selected from the group consisting of: SEQ ID NO:6, SEQ ID NO:7, and SEQ ID NO:8.

18. The recombinant *Lactococcus lactis* bacterial cell of claim 13, wherein the nucleotide sequence is operably linked to a composite promoter comprising SEQ ID NO:6, SEQ ID NO:7, and SEQ ID NO:8.

19. A recombinant *Lactococcus lactis* bacterial cell comprising a nucleotide sequence coding for enterotoxigenic *Escherichia coli* colonization factor antigen I fimbriae genes cfaA, cfaB, cfaC, and cfaE, wherein the bacterial cell expresses *E. coli* colonization factor antigen I fimbriae genes comprising cfaA, cfaB, cfaC, and cfaE; wherein the nucleotide sequence comprises a polynucleotide sequence sharing at least 95% sequence identity with SEQ ID NO:1.

20. The recombinant *Lactococcus lactis* bacterial cell of claim 19, wherein the polynucleotide sequence shares 100% sequence identity with SEQ ID NO:1.

21. A method for producing a composition for the treatment of an autoimmune or inflammatory disease, the method comprising:
(a) introducing a nucleotide sequence coding for enterotoxigenic *Escherichia coli* colonization factor antigen I fimbriae genes into a recipient *Lactococcus lactis* bacterial cell, wherein the antigen I fimbriae genes comprise cfaA, cfaB, cfaC, and cfaE; and wherein the nucleotide sequence comprises a polynucleotide sequence sharing at least 95% sequence identity with SEQ ID NO:1.

22. The method of claim 21, wherein the polynucleotide sequence shares 100% sequence identity with SEQ ID NO:1.

23. The method of claim 21, further comprising:
(b) culturing the bacterial cell under conditions which allow for expression of the enterotoxigenic *Escherichia coli* colonization factor.

* * * * *